US006649635B2

(12) United States Patent
McMahon et al.

(10) Patent No.: US 6,649,635 B2
(45) Date of Patent: Nov. 18, 2003

(54) HETEROARYLCARBOXAMIDE COMPOUNDS ACTIVE AGAINST PROTEIN TYROSINE KINASE RELATED DISORDERS

(75) Inventors: Gerald McMahon, Kenwood, CA (US); Peng Cho Tang, Moraga, CA (US); Laura Kay Shawver, San Francisco, CA (US); Klaus Peter Hirth, San Francisco, CA (US)

(73) Assignee: Sugen, Inc., South San Francisco, CA (US)

(*) Notice: Subject to any disclaimer, the term of this patent is extended or adjusted under 35 U.S.C. 154(b) by 0 days.

(21) Appl. No.: 09/948,090

(22) Filed: Sep. 7, 2001

(65) Prior Publication Data

US 2002/0065283 A1 May 30, 2002

Related U.S. Application Data

(62) Division of application No. 09/081,917, filed on May 19, 1998, now Pat. No. 6,316,479.
(60) Provisional application No. 60/047,084, filed on May 19, 1997.

(51) Int. Cl.$^7$ ............... A61K 31/443; C07D 413/12
(52) U.S. Cl. ................. 514/340; 546/272.1
(58) Field of Search .............. 546/272.1; 514/340

(56) References Cited

U.S. PATENT DOCUMENTS

| | | | | |
|---|---|---|---|---|
| 4,087,535 A | 5/1978 | Heubach et al. | ............ | 424/272 |
| 4,284,786 A | 8/1981 | Kammerer et al. | ......... | 548/248 |
| 4,351,841 A | 9/1982 | Kammerer et al. | ......... | 424/272 |
| 4,965,276 A | 10/1990 | Bartlett et al. | ............. | 514/378 |
| 4,992,271 A | 2/1991 | Fernandez et al. | ......... | 424/85.2 |
| 5,217,999 A | 6/1993 | Levitzki et al. | ............ | 514/613 |
| 5,268,382 A | 12/1993 | Bartlett et al. | ............. | 514/378 |
| 5,314,685 A | 5/1994 | Tyle et al. | ................... | 424/401 |
| 5,371,099 A | 12/1994 | Bartlett et al. | ............. | 514/378 |
| 5,403,858 A | 4/1995 | Bastard et al. | ............. | 514/449 |
| 5,476,866 A | 12/1995 | Kuo et al. | ................. | 514/378 |
| 5,494,911 A | * 2/1996 | Bartlett et al. | ............. | 514/256 |
| 5,514,711 A | 5/1996 | Kitano et al. | .............. | 514/521 |
| 5,532,259 A | 7/1996 | Bartlett et al. | ............. | 514/378 |
| 5,547,971 A | 8/1996 | Weithmann et al. | ........ | 514/378 |
| 5,573,775 A | 11/1996 | Robertson et al. | ......... | 424/427 |
| 5,610,173 A | 3/1997 | Schwartz et al. | ........... | 514/378 |
| 5,700,822 A | 12/1997 | Hirth et al. | ................ | 514/380 |
| 5,700,823 A | 12/1997 | Hirth et al. | ................ | 514/380 |
| 5,783,592 A | 7/1998 | Schwartz et al. | ........... | 514/378 |
| 5,843,947 A | * 12/1998 | Robert et al. | ............... | 514/252 |
| RE36,256 E | 7/1999 | Spada et al. | ................ | 514/249 |
| 5,932,602 A | 8/1999 | Hirth et al. | ................ | 514/380 |
| 5,958,959 A | 9/1999 | Hirth et al. | ................ | 514/378 |
| 5,990,141 A | 11/1999 | Hirth et al. | ................ | 514/380 |
| 6,020,372 A | * 2/2000 | Schwab et al. | ............. | 514/521 |
| 6,022,884 A | * 2/2000 | Mantlo et al. | .............. | 514/352 |
| 6,184,237 B1 | * 2/2001 | Mantlo et al. | .............. | 514/335 |
| 6,187,797 B1 | * 2/2001 | Pruitt et al. | ................. | 514/340 |
| 6,316,479 B1 | * 11/2001 | McMahon et al. | .......... | 514/378 |
| 6,333,341 B1 | * 12/2001 | Mantlo et al. | .............. | 514/336 |

FOREIGN PATENT DOCUMENTS

| | | |
|---|---|---|
| AU | 3101093 | 1/1993 |
| DE | 2524929 | 12/1976 |
| EP | 0359184 | 9/1989 |
| EP | 0413329 | 2/1991 |
| EP | 0520722 | 6/1992 |
| EP | 0522937 | 7/1992 |
| EP | 0537742 | 4/1993 |
| EP | 0551230 | 7/1993 |
| EP | 0607775 | 7/1994 |
| EP | 0607776 | 7/1994 |
| EP | 0607777 | 7/1994 |
| EP | 0645145 | 9/1994 |
| EP | 0665013 | 2/1995 |
| EP | 0 769 296 | 4/1997 |
| EP | 0804191 | 5/2000 |
| GB | 2240104 | 7/1991 |
| WO | 8704436 | 7/1987 |
| WO | 9117748 | 11/1991 |
| WO | 9221641 | 4/1992 |
| WO | 9218481 | 10/1992 |
| WO | 9220642 | 11/1992 |
| WO | 9202444 | 4/1993 |
| WO | 9426260 | 11/1994 |
| WO | 9519169 | 7/1995 |
| WO | 9521613 | 8/1995 |
| WO | 96/33179 | 10/1996 |
| WO | 99/10325 | 3/1999 |

OTHER PUBLICATIONS

Bartlett et al., Chemical Abstracts, vol. 116:128908, 1992.*
Robert et al., Chemical Abstracts, vol. 124:202306, 1996.*
Schwab et al., Chemical Abstracts, vol. 126:325499, 1997.*
Pruitt et al., Chemical Abstracts, vol. 134:163023, 2001.*
Rying et al., Chemical Abstracts, vol. 127:121701, 1997.*
Coghlan et al., Chemical Abstracts, vol. 123:285992, 1995.*
Park et al., Chemical Abstracts, vol. 114:81672, 1991.*
Mandal et al., Chemical Abstracts, vol. 106:138320, 1987.*
Kaemmerer et al., Chemical Abstracts, vol. 89:109449, 1978.*
Mantlo et al., Chemical Abstracts, vol. 130:352186, 1999.*
Aas et al., "Chloropromazine in combination with nitrosourea inhibits experimental glioma growth," *British Journal of Neurosurgery* 8(2):187–192 (1994).
Andrews et al. (American Veterinary Medicine Association Panel on Euthana), "1993 Report of the AVMA Panel on Euthanasia," *J. American Veterinary Medicine Association* 202(2):229–249 (1993).
Bartlett et al., "Leflunomide (HWA 486), a novel immunomodulating compound for the treatment of autoimmune disorders and reactions leading to transplantation rejection," *Agents and Actions* 32:10–21 (1991).

(List continued on next page.)

Primary Examiner—Richard L. Raymond
(74) Attorney, Agent, or Firm—Beth A. Burrous; Foley & Lardner

(57) ABSTRACT

The present invention relates to novel heteroarylcarboxamides which modulate the activity of protein tyrosine kinases and therefore are expected to be useful in the treatment of abnormal protein tyrosine kinase activity driven disorders including cancer.

24 Claims, No Drawings

OTHER PUBLICATIONS

Bartlett et al., "Effects of leflunomide on immune responses and models of inflammation," *Springer Semin. Immunopathol.* 14:381–394 (1993).

Bartlett et al., "Leflunomide: A novel immunomodulating drug in Nonsteroidal Anti–Inflammatory Drugs" 2nd ed. pp. 349–366, Lewis and Furstk eds., Dekker, NY, (1985).

Baselga et al., "Antitumor Effects of Doxorubicin in Combination With Anti–epidermal Growth Factor Receptor Monoclonal Antibodies," *J. of Natl. Cancer Institute* 85(16):1327–1333 (1993).

Baudy et al., "Potent Quinoxaline–Spaced Phosphono alpha–Amino Acids of the AP–6 Type as Competitive NMDA Antagonists: Synthesis and Biological Evaluation," *J. Med. Chem.* 36:331–342 (1993).

Bilder et al., "Tyrphostins inhibit PDGF–induced DNA synthesis and associated early events in smooth muscle cells," *Am. J. Physiol.* 260(Cell Physiol.29): C721–C730 (1991).

Birchall et al., "Compositions for killing internal parasites containing 3–teri–alkyl–4–hydroxy–5–halobenzylidene–malononitriles," *Chemical Abstracts* 88:535 (1978).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bustelo and Barbacid, "Tyrosine Phosphorylation of the vav Proto–Incogene Product in Activated B Cells," *Science* 256: 1196–1199 (1992).

Caraglia et al., "Cytosine arabinoside increases the binding of 125 I–labelled epidermal growth factor and 125 I–transferrin and enhances the in vitro targeting of human tumour cells with anti–(growth factor receptor)mAb," *Cancer Immunol. Immunother.* 37:150–156 (1993).

Carboni et al., "Cyanocarbon Chemistry. XI. Malononitrile Dimer," *J. Am. Chem. Soc.* 80:2838–2840 (1958).

*Cecil Textbook of Medicine,* Eds: Wyngaarden, Smith, Bennett, W.B. Saunders p. 2220, (1992).

Charette et al., "Contemporary approaches of chemotherapy," *Neuro–Oncology,* 7(1):135 (1995).

Chen and Okayama, "Calcium Phosphate–Mediated Gene Transfer: A Highly Efficient Transfection System for Stably Transforming Cells with Plasmid DNA," *BioTech.* 6:632–638 (1988).

Cherwinski et al., "The Immunosuppressant Leflunomide Inhibits Lymphocyte Progression Through Cell Cycle by a Novel Mechanism," *J. Pharmacology and Exp. Therap.* 227:460–468 (1995).

Chong et al., "Leflunomide, A Novel Immunosuppressive Agent," *Transplantation* 55:1361–1366 (1993).

Chong et al., "Leflunomide, A Novel Immunomodulatory Agent: In Vitro Analyses of the Mechanism of Immunosuppression," *Transplant. Proc.* 25:747–749 (1993).

Conn et al., "Purification of a glycoprotein vascular endothelial cell mitogen from a rat glimo–derived cell line," *Proc. Natl. Acad. Sci. USA* 87:1323–1327 (1990).

Dati et al., "Inhibition of c–erB–2 oncogene expression by estrogens in human breast cancer cells," *Oncogene* 5:1001–1006 (1990).

Decker and Lohmann–Matthes, "A quick and simple method for the quantitation of lactate dehydroganse release in measurements of cellular cytotoxicity and tumor necrosis factor (TNF) activity," *J. Immunol. Methods* 115:61–69 (1988).

Ehrlich and Bogert, "Experiments in the Veratrole and Quinoxaline Groups," *J. Org. Chem.* 12:522 (1947).

Ferris et al., "Synthesis of Zuinazoline Nucleosides from Ribose and Anthranilonitrile. Application of Phase–Transfer Catalysis in Nucleoside Synthesis," *J. Org. Chem.* 44(2):173–178 (1979).

Finlay, "The role of high–dose chemotherapy and stem cell rescue in the treatment of malignant brain tumors," *Bone Marrow Transplantation* 18(Suppl. 3):S1–S5 (1996).

Floege et al., "Factors involved in the regulation of mesangial cell proliferation in vitro and in vivo," *Kidney International* 43S:47–54 (1993).

Fry et al., "New insights into protein–tyrosine kinase receptor signaling complexes," *Protein Science* 2:1785–1797 (1993).

Gazit et al., "Tyrphostins. 1. Synthesis and Biological Activity of Protein Tyrosine Kinase Inhibitors," *J. Med. Chem.* 32:2344–2352 (1989).

Gazit et al., "Tyrophostins. 2. Heterocyclic and alpha–Substituted Benzylidenemalononitrile Tyrphostins as Potent Inhibitors of EGF Receptor and ErbB2/neu Tyrosine Kinases," *J. Med. Chem.* 34:1896–1907 (1991).

Gazit et al., "Tyrphostins. 3. Structure–Activity Relationship Studies of a .alpha.–Substituted Benzylidenemalonoitrile 5–S–Aryltyrphostins" *J. Med. Chem.* 36:3556–3564 (1993).

Glant et al., "Immunomodulation of proteoglycan–induced progressive polyarthritis by leflunomide," *Immunopharmacology* 23:105–116 (1992).

Gottardis et al., "Estradiol–Stimulated Growth of MCF–7 Tumors Implanted in Athymic Mice: A Model to Study the Tumoristatic Action of Tamoxifen," *J. Steroid Biochem.* 30(1–6):331–314 (1988).

Gulbins et al., "Tyrosine Kinase–Stimulated Guanine Nucleotide Exchange Activity of Vav in T Cell Activation," *Science* 260:822–825 (1993). Hale et al., "Prognostic value of epidermal growth factor receptor expression in cervical carcinoma," *J. Clin. Pathol.* 46:149–153 (1993).

Hambleton and Mahon, "Drug actions on delayed–type hypersensitivity in rats with developing and established adjuvant arthritis" *Agents and Actions* 29:328–332 (1990).

Harris et al., "Breast Cancer (First of Three Parts)," *New England J. of Medicine* 327(5):319–328 (1992).

Heldin, "Structural and functional studies on platelet–derived growth factor," *EMBO Journal* 11:4251–4259 (1992).

Hochberg et al., "Treatment of recurrent malignant glioma with BCNU–fluosol and oxygen inhalation. A phase I–II study," *Neuro–Oncology* 32(1):45–55 (1997).

Hoekstra et al., "Differential effects of steurosporine and tyrphostins on receptor tyrosine kinase autophosphorylation and peptide substrate phosphorylation," *Experimental Therapeutics from 84th Annual Meeting of American Association for Cancer Research,* vol. 34, #2455 (1993).

Honegger et al., "Point Mutation at the ATP Binding Site of EGF Receptor Abolishes Protein–Tyrosine Kinase Activity and Alters Cellular Routing," *Cell* 5:199–209 (1987).

Houck et al., "The Vascular Endothelial Growth Factor Family: Identification of a Fourth Molecular Species and Characterization of Alternative Splicing of RNA," *Molecular Endocrinology* 5:1806–1814 (1991).

Issidorides and Haddadin, "Benzofurazan Oxide. II. Reactions with Enolate Anions," *J. Org Chem.* 31:4067–4068 (1966).

Ju et al., "Leflunomide inhibits cytokine–induced DNA synthesis of rabbit synovial cells in culture," *Acta Pharmacological Sinica* 15:2232–26 (1994).

Ju et al., "Leflunomide inhibits PAF induced DNA synthesis in rabbit synovial cells and PAF production from rat peritomeal macrophages," *Acta Pharmacological Sinica* 92:90–94 (1994).

Karameris et al., "Expression of Epidermal Growth Factor (EGF) and Epidermal Growth Factor Receptor (EGFR) in Gastric and Colorectal Carcinomas, An Immunohistological Study of 63 Cases," *Path. Res. Pract.* 189:133–137 (1993).

Kaur, "Tyrophostin induced growth inhibitions: correlation with effort on p210.bcr–abl autokinase activity in K562 chronic myelogenous leukemia," *Anti–Cancer Drugs* 5:213–222 (1994).

Kiu et al., "combination chemotherapy with carmustine and cisplatin before, during, and after radiotherapy for adult malignant gliomas," *Neuro–oncology* 25(3):215–220 (1995).

Koenders et al., "Epidermal growth factor receptor and prognosis in human breast cancer: a prospective study," *Breast Cancer Research and Treatment* 25:21–27 (1993).

Korzeniewski and Callewaert, "An Enzyme–Release Assay for Natural Cytotoxicity," *J. Immunol. Methods* 64:313 (1983).

Kovalenko et al., "Selective Platelet–derived Growth Factor Receptor Kinase Blockers Reverse sis–Transformation," *Cancer Research* 54:6106–6114 (1994).

Kuechle et al., "Prevention of Kidney and Skin Graft Rejection in Rats by Leflunomide, a New Immunomodulating Agent," *Transplant Proc.* 23:1083–1806 (1991).

Kurpad et al., "Intraarterial $O^6$–benzylguanine enables the specific therapy of nitrosourea–resistant intracranial human glioma xenografts in athymic rats with 1,3–bis(2–chloroethyl)–1–nitrosourea," *Cancer Chemotherapy and Pharmacology* 39(4):307–316 (1997).

Lee and Salemnick, "Purine N–Oxides, LXII. 2,4–Dioxophyrido–2,3–d–pyrmidine N–Oxides," *J. Org. Chem.* 40(24):3608–3610 (1975).

Levitzki, "Tyrphostins—Potential Antiproliferative Agents and Novel Molecular Tools," *Biochem. Pharm.* 40(5):913–918 (1990).

Ley and Seng, "Synthesis unter Verwendung von Benzofuroxan," *Synthesis* 1975:415–422 (1975).

Lyall et al., "Tyrphostins Inhibit Epidermal Growth Factor (EGF)–Receptor Tyrosine Kinase Activity in Living Cells and EGF–stimulated Cell Proliferation," *J. Bio. Chem.*, 264:14503–14509 (1989).

Malkin et al., "Phase I study of SU101, a novel signal transduction inhibitor, in recurrent malignant glioma," *Proc Annu. Meet Am. Soc. Clin. Oncol.* 16:A1371 (1997).

Marshall, E., "Search for a Killer: Focus Shifts from Fat to Hormones," *Science* 259:618–621 (1993).

Mattar et al., "Inhibition of the epidermal growth factor receptor tyrosine kinase activity to leflunomide," *FEBS Letters* 334 (2):161–164 (1993).

Mattar et al.,, "Effect of leflunomide active metabolite, A771726, on signal transduction pathways necessary for proliferation," *Immunobiology* 186(1–2):43 (1992) (abstract).

McChesney et al., "An Evaluation of Leflunomide in the Canine Real Transplantation Model," *Transplantation* 57:1717–1722 (1994).

Millauer et al., "High Affinity VEGF Binding and Developmental Expression Suggest Flk–1 as a Major Regulator of Vasculogenesis and Angiogenesis," *Cell* 72:835–846 (1993).

Mosmann, "Rapid Colorimetric Assay for Cellular Growth and Survival: Application to Proliferation and Cytotoxicity Assays," *J. Immunol. Methods* 65:55–63 (1983).

Muller et al., "BCR First Exon Sequences Specifically Activate the BCR/ABL Tyrosine Kinase Oncogene of Philadelphia Chromosome–Positive Human Leukemias," *Mol Cell. Biol.* 11:1785–1792 (1991).

Nichterlein et al., "Leflunomide (HWA 486) Prolongs Course of Murine Listeriosis," *Immunol. Infect. Dis.* 4:18–22 (1994).

Ogawa et al., "Therapeutic Effects of Leflunomide, a New Antirheumatic Drug, on Glomerulonephritis Induced by the Antibasement Membrane Antibody in Rats," *Clin. Immunol. Immunopath.* 61:103–118 (1991).

Ogawa et al., "Effects of leflunomide on glomerulonephritis induced by antibasement membrane antibody in rats," *Agents Actions* 31:321–328 (1990).

Ohmichi et al., "The Tyrosine Kinase Inhibitor Tyrphostin Blocks the Cellular Actions of Nerve Growth Factor," *Biochemistry* 32:4650–4658 (1993).

Osborne et al., "Effect of Estrogens and Antiestrogens on Growth of Human Breast Cancer Cells in Athymic Nude Mice," *Cancer Research* 45:584–590 (1985).

Osherov et al., "Selective Inhibition of the EGF and Neu receptors by Tyrophostins," *J. Cell Biochem.* S17A:237 (1993).

Osherov et al., "Selective Inhibition of the Epidermal Growth Factor and HER2/Neu Receptors by Tyrphostins," *J. Bio. Chem.* 268:11134–11142 (1993).

Ozzelo and Sordat, "Behavior of Tumors Produced by Transplantation of Human Mammary Cells Lines in Athymic Nude Mice," *Eur. J. Cancer* 16:553–559 (1980).

Patterson et al., "3–Carboxy–5–methyl–N–4–(trifluoromethyl)phenyl–4–isoxazolecarboxamide, a New Prodrug for the Antiarthritic Agent 2–Cyano–3–hydroxy–N–4–(trifluoromethyl) phenyl–2–butenamide," *J. Med. Chem.* 35:507–520 (1992).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Pigott et al., "Expression of epidermal growth factor receptor in human glioblastoma multiforme," *Brit. J. of Neurosurgery* 7:261–265 (1993).

Plate et al., "Vascular endothelial growth factor is a potential tumour angiogenesis factor in human gliomas in vivo," *Nature* 359:845–848 (1992).

Plate et al., "Up–Regulation of Vascular Endothelial Growth Factor and Its Cognate Receptors in a Rat Glioma Model of Tumor Angiogenesis," *Cancer Research* 53:5822–5827 (1993).

Plate et al., "Platelet–Derived Growth Factor Receptor–beta is Induced during Tumor Development and Upregulated during Tumor Progression in Endothelial Cells in Human Gliomas," *Laboratory Investigation* 4:529–534 (1992).

Plowman et al., "Preclinical antitumor activity of temozolomide in mice: Efficacy against human brain tumor xenografts and synergism with 1,3–Bis(2–chloroethyl)–1–nitrosourea" *Cancer Research* 54(14):3793–3799 (1994).

Pollack et al., "Response of malignant glioma cell lines to epidermal growth factor and platelet–derived growth factor in a serum–free medium," *J. Neurosurg.* 73:106–112 (1990).

Ren et al., "Identification of a Ten–Amino Acid Proline–Rich SH3 Binding Site," *Science* 259:1157–1161 (1993).

Rendu et al., "Inhibition of Platelet Activation by Tyrosine Kinase Inhibitors," *Biochem. Pharm.* 44(5):881–888 (1992).

Rosen et al., "A phase I/II study of SU101 in patients with ovarian, prostate, and non–small cell lung cancers," *Proc. Annu. Meet. Am. Soc. Clin. Oncol.* 16:A739 (1997).

Rosenthal et al., "Conditioned Medium from Mouse Sarcoma 180 Cells Contains Vascular Endothelial Growth Factor," *Growth Factors* 4:53–59 (1990).

Ross, "The pathogenesis of atherosclerosis: a perspective for the 1990's," *Nature* 362:801–809 (1993).

Rusch et al., "Differential Expression of the Epidermal Growth Factor Receptor and Its Lgands in Primary Non–Small Cell Lung Cancers and Adjacent Benign Lung," *Cancer Research* 53:2379–2385 (1993).

Rygaard and Povlsen, "Heterotransplantation of a Human Malignant Tumour to Nude Mice," *Acta Path. Microbiol. Scand.* 77:758–760 (1969).

Satou Fumihiro "Injection Containing Etoposide," Application No. JP60239415 published Nov. 28, 1995.

Schorlemmer et al., "Prolongation of Allogeneic Transplanted Skin Grafts and Induction of Tolerance by Leflunomide, A New Immunosuppressive Isoxazol Derivative," *Transplant. Proc.* 25:763–767 (1993).

Schornagel et al., "Synthesis and Evaluation of 2,4–Diaminoquinazoline Antioflates with Activity Against Methotrexate–Resistant Human Tumor Cells," *Biochem. Pharm.* 33(20):3251–3255 (1984).

Scott et al., "p185.HER2 Signal Transduction in Breast Cancer Cells," *J. Bio. Chem.* 266(22):14300–14305 (1991).

Seibert et al., "Clonal Variation of MCF–7 Breast Cancer Cells in Vitro and in Athymic Nude Mice," *Cancer Research* 43:2223–2239 (1983).

Shafie and Grantham, "Role of Hormones in Growth and Regression of Human Breast Cancer Cells (MCF–7) Transplanted into Athymic Nude Mice," *J. Natl. Cancer Institute* 67(1):51–56 (1981).

Shweiki et al., "Vascular endothelial growth factor induced by hypoxia may mediate hypoxia–initiated angiogenesis," *Nature* 359:843–845 (1992).

Skehan et al., "New Colorimetric Cytotoxicity Assay for Anticancer–Drug Screening," *J. Natl. Cancer Inst.* 82:1107–1112 (1990).

Talmadge and Twardzik, "Role of Cytokines in Inflammation and Autoimmunity," *Agents and Actions* 35S:135–141 (1991).

Thoenes et al., "Leflunomide (HWA 486) Inhibits Experimental Autoimmune Tubulointerstitial Nephritis in Rats," *Int. J. Immunopharmacol.* 11:921–929 (1989).

Ueno et al., "Inhibition of PDGF beta Receptor Signal Transduction by Coexpression of a Truncated Receptor," *Science* 252:844–252 (1991).

Ulrichs et al., "Suppression of Natural Xenophile Antibodies With the Novel Immunomodulating Drug Leflunomide," *Transplant. Proc.* 24:718–719 (1992).

Van der Wall et al., "High–dose chemotherapy regimens for solid tumors," *Cancer Treatment Reviews* 21(2):105–132 (1995).

Van Ummersen et al., "A phase I trial of SU101 in patients with solid tumors," *Proc. Annu. Meet. Am. Soc. Clin. Oncol.* 16:A740 (1997).

Wada et al., "Anti–receptor antibodies reverse the phenotype of cells transformed by two interacting proto–oncogene encoded receptor proteins," *Oncogene* 5:489–495 (1990).

Waltenberger et al., "Different Signal Transduction Properties of KDR and Flt1, Two Receptors for Vascular Endothelial Growth Factor," *J. Biol. Chem.* 269:26988–26995 (1994).

Warri et al., "Estrogen Suppression of erbB2 Expression is Associated with Increased Growth Rate of ZR–75–1 Human Breast Cancer Cells In Vitro and in Nude Mice," *Int. J. Cancer* 49:616–623 (1991).

Wedge et al., "$O^6$–benzylguanine enhances the sensitivity of a glioma xenograft with low $O^6$–axlkylguanine–DNA alkyltransferase activity to temozolomide and BCNU," *British Journal of Cancer* 73(9):1049–1052 (1996).

Weithmann et al., "Effect of leflunomide on constitutive and inducible pathways of cellular eiconsanoid generation," *Agents Actions* 41:164–170 (1994).

Williams et al., "Immunosuppressive Effects of Leflunomide in a Cardiac Allograft Model," *Transplantation Proc.* 25:745–746 (1993).

Williams et al., "Leflunomide in Experimental Transplantation," *Transplantation* 57:1223–1231 (1994).

Xiao et al., "Effect of Leflunomide in Control of Acute Rejection in Hamster–to–Rat Cardiac Xenografts," *Transplantation Proceedings* 26:1263–1265 1994).

Xiao et al., "Leflunomide Controls Rejection in Hamster to Rat Cardiac Xenografts," *Transplantation* 58:828–834 (1994).

Yaish et al., "Blocking of EGF–Dependent Cell Proliferation by EGF Receptor Kinase Inhibitors," *Science* 242:933–935 (1988).

Yoneda et al., "The Antiproliferative Effects of Tyrosine Kinase Inhibitors Tyrphosins on a Human Squamous Cell Carcinoma in Vitro and in Nude Mice," *Cancer Research* 51:4430–4435 (1991).

Zeillinger et al., "EGF–R and Steroid Receptors in Breast Cancer: A Comparison with Tumor Grading, Tumor Size, Lymph Node Involvement, and Agent" *Clin. Biochem.* 26:221–227 (1993).

Zielinski et al., "Effects of leflunomide (HWA 486) on expression of lymphocyte activation markers," *Agents Actions* 38:(Special Conference Issue) C80–C82 (1993).

Myers et al., See Abs. Attached, Curr. Pharm. Design, 3/5, 1997.

Dainippon Pharm., Chemical Abstracts, vol. 72:12709, 1970.

Jaschke et al., Chemical Abstracts, vol. 120:217654, 1994.

White, Chemical Abstracts, vol. 111:227133, 1989.

Los Mario, Chemical Abstracts, vol. 102:45926, 1985.

Palomo Coll, Chemical Abstracts, vol. 85:62229, 1976.

* cited by examiner

HETEROARYLCARBOXAMIDE COMPOUNDS ACTIVE AGAINST PROTEIN TYROSINE KINASE RELATED DISORDERS

RELATED APPLICATIONS

This Application is a Divisional of application Ser. No. 09/081,917, filed on May 19, 1998, now U.S. Pat. No. 6,316,479, which claims priority from Provisional Application Serial No. 60/047,084, filed May 19, 1997, both of which are incorporated by reference as if fully set forth herein.

The present invention relates generally to organic chemistry, biochemistry, pharmacology and medicine. More particularly, it relates to novel heterocyclic compounds, and their physiologically acceptable salts, which modulate the activity of protein tyrosine kinases which are involved in the control of cell proliferation, differention and growth and therefore are expected to exhibit a salutary effect against disorders related to abnormal protein tyrosine kinase activity.

BACKGROUND OF THE INVENTION

The following is offered as background information only and is not admitted to be prior art to the present invention.

Cellular signal transduction is a fundamental mechanism whereby external stimuli that regulate diverse cellular processes are relayed to the interior of cells. Growth factor receptors ("Gfrs") are an important part of the signal transduction pathway. Gfrs are cell-surface proteins. When bound by a growth factor ligand, Gfrs are converted to an active form which interacts with proteins on the inner surface of a cell membrane. As the result of this interaction, one of the key biochemical mechanisms of signal transduction is initiated; i.e., the reversible phosphorylation of various proteins within the cell. This phosphorylation of intra-cellular proteins causes the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron*, 9:303–391 (1992). See also, Posada and Cooper, *Mol. Biol. Cell.*, 3:583–392 (1992) and Hardie, *Symp. Soc. Exp. Biol.*, 44:241–255 (1990).

The molecules which effect the phosphorylation of proteins are called protein kinases ("PKs"). One of the classes of PKs, which is of particular importance to the present invention, phosphorylates proteins on the alcohol moiety of serine, threonine and tyrosine residues in eukariotic cells. These PKs fall essentially into two groups, those specific for phosphorylating serines and threonines, and those specific for phosphorylating tyrosines. The protein tyrosine kinases ("PTKs") can be further divided into receptor PTKs, abbreviated "receptor tyrosine kinases" or "RTKS" and non-receptor PTKs, sometimes refered to as "cellular tyrosine kinases" or "CTKs."

The RTKs are comprised of an extracellular glycosylated ligand binding domain, a transmembrane domain and an intracellular cytoplasmic catalytic domain that can phosphorylate tyrosine residues on proteins. On the other hand CTKs are entirely intra-cellular and do not contain extracellular and transmembrane domains.

PTKs play an important role in the control of cellular processes including proliferation, differentiation, migration and survival. Enhanced PTK activity due to activating mutations or overexpression has been implicated in many human cancers. It is clear from numerous studies (q.v, infra) that the activity of PTKs must be tightly controlled in normal cells and healthy tissue, as mutations resulting in overactivity of PTKs cause diseases that are associated with excessive cell growth and proliferation while mutations which result in reduction or loss of activity can cause; e.g., embryonal lethality or developmental disorders.

The RTKs comprise one of the larger families of PTKs and have diverse biological activity. At present, at least nineteen (19) distinct subfamilies of RTKs have been identified. One such subfamily is the "HER" family of RTKS, which include EGFR (epithelial growth factor receptor), HER2, HER3 and HER4. These, RTKs consist of an extracellular glycosylated ligand binding domain, a transmembrane domain and an intracellular cytoplasmic catalytic domain that can phosphorylate tyrosine residues on proteins. One well-known example of the apparent involvement of PTKs/RTKs in cellular disorders is the association of Her2 over-expression with breast cancer (Slamon, et al., *Science*, 244:707 (1989).

Another RTK subfamily consists of insulin receptor (IR), insulin-like growth factor I receptor (IGF-1R) and the insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domains is interrupted by unrelated amino acid sequences.

Another group which, because of its similarity to the PDGFR subfamily, is sometimes subsumed in the later group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1).

Finally, the FGFR family of PTKs contains at least four distinct members: FGFR1 (also called Flg and Cek1), FGFR2 (also called Bek, Ksam, KsamI and Cek3), FGFR3 (also called Cek2) and FGFR4. They share a common structure consisting of, in the mature protein, one or more immunoglobulin-like (IgG-like) loops flanked by characteristic cysteines, a hydrophobic transmembrane domain and a intracellular domain containing a catalytic region that is split by a short insert; See Ullrich and Schlessinger, *Cell*, 61:203 (1990).

A more complete listing of the known RTK subfamilies is described in Plowman et al., *DN&P*, 7(6):334–339 (1994) which is incorporated by reference, including any drawings, as if fully set forth herein.

At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene*, 8:2025–2031 (1993), which is incorporated by reference, including any drawings, as if fully set forth herein.

Both RTKs and CTKs have been implicated in a host of pathogenic conditions including, significantly, cancer.

Other pathogenic conditions to which RTKs and CTKs have been linked include, without limitation, psoriasis, hepatic cirrhosis, diabetes, atherosclerosis, arterial restinosis, kidney sclerosis, wound scarring and a variety of renal disorders.

With regard to cancer, two of the major hypotheses advanced to explain the excessive cellular proliferation that drives tumor development relate to functions known to be PTK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs) and cytoplasmic PTKs (CTKs), discussed above.

In view of the apparent link between PTK-related cellular activities and a number of virulent human disorders, it is no surprise that a great deal of effort is being expended in an attempt to identify ways to modulate PTK activity. Some of these have involved biomimetic approaches using large molecules patterned on those involved in the actual cellular processes (e.g., mutant ligands (U.S. Pat. No. 4,966,849)); soluble receptors and antibodies (App. No. WO 94/10202, Kendall and Thomas, *Proc. Nat'l Acad. Sci.*, 90:10705–09 (1994), Kim, et al., *Nature*, 362:841–844 (1993)); RNA ligands (Jelinek, et al., *Biochemistry*, 33:10450–56); Takano, et al., *Mol. Bio. Cell* 4:358A (1993); Kinsella, et al., *Exp. Cell Res.* 199:56–62 (1992); Wright, et al., *J. Cellular Phys.*, 152:448–57)) and tyrosine kinase inhibitors (WO 94/03427; WO 92/21660; WO 91115495; WO 94/14808; U.S. Pat. No. 5,330,992; Mariani, et al., *Proc. Am. Assoc. Cancer Res.*, 35:2268 (1994)).

More recently, attempts have been made to identify small molecules which act as PTK inhibitors. For example, bis-monocylic, bicyclic and heterocyclic aryl compounds (PCT WO 92/20642), vinylene-azaindole derivatives (PCT WO 94/14808 and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as compounds for use as PTK inhibitors for use in treatment of cancer.

SUMMARY OF THE INVENTION

Our own efforts to identify small organic molecules which modulate PTK activity and which, therefore, should be useful in the treatment and prevention of disorders driven by abnormal PTK activity, has led us to the discovery of novel heteroarylcarboxamide compounds which modulate PTK activity and which are the subject of this invention.

Thus, in one aspect, the present invention relates to novel heteroarylcarboxamides which modulate the activity of PTKs. In addition, the present invention relates to the preparation and use of pharmacological compositions of the disclosed compounds and their physiologically acceptable salts in the treatment and prevention of PTK driven disorders.

As used herein, a "heteroarylcarboxamide" refers generally to a "C-amido" group, as defined herein, where the "C" carbon is covalently bonded to a carbon atom of a "heteroaryl" group, also as defined herein, $R^{12}$ is hydrogen and $R^{13}$ is selected from the "aryl" and "heteroaryl" groups defined, infra.

It is understood that when Z, q.v., infra, is sulfur, the compound will formally be a heteroarylthiocarboxamide; however, whenever the term heteroarylcarboxamide is used herein, it will refer to the sulfur analog as well.

A "pharmacological composition" refers to a mixture of one or more of the compounds described herein, or a physiologically acceptable salt thereof, with other chemical components, such as pharmaceutically acceptable carriers and excipients. The purpose of a pharmacological composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmacological composition to further facilitate administration of a compound. Examples, without limitation, of excipients include calcium carbonate, calcium phosphate, various sugars and types of starch, cellulose derivatives, gelatin, vegetable oils and polyethylene glycols.

1. THE COMPOUNDS 4-(-(4'-trifluoromethylphenyl) carboxamido)-5-methyl-isoxazole ("leflunomide", Formula 1), to which the compounds of the present invention are structurally related, is a compound currently in clinical testing, based on its ability to inhibit unwanted cell proliferation, both as an immunosuppressive and a cancer drug. Leflunomide is believed to be metabolized in serum such that the isoxazole ring is converted to an open form called in the literature A771726 and having the chemical structure shown in Formula 2.

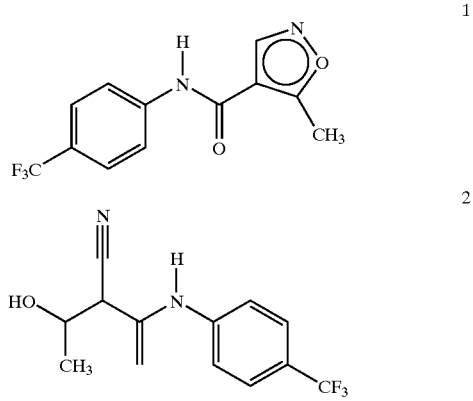

Several early reports suggested that leflunomide was capable of inhibiting tyrosine kinase signaling (Bartlett, et al., *Agents and Actions*, 32:10 (1991), Mattar, et al., *FEBS Lett.*, 334:161 (1993), Xu, et al., *J. Biol. Chem.*, 270:12398 (1995)). More recently Cherwinski, et al. reported that leflunomide has no effect on tyrosine kinase signaling but inhibited proliferation by inhibiting DNA replication and entry of cells into M-phase of the cell cycle (*J. Pharma. and Exp. Thera.*, 272:460 (1995)). Subsequent reports have suggested that the activity of leflunomide is solely due to the ability of A771726 to inhibit pyrimidine biosynthesis by inhibiting a key enzyme in that process, dihydro-orotate dehydrogenase (DHOD) (Nair, et al., *Imm. Lett.*, 47:171

(1995), Greene, et al., *Biochem. Pharma.*, 50:861 (1995), Cherwinski, et al., *Inflamm. Res.*, 44:317 (1995), Davis et al., *Biochem.*, 35:1270 (1996)). Thus it has been widely accepted in the art that leflunomide acts only as a prodrug.

The ability of A771726 to inhibit pyrimidine biosynthesis is overcome by the addition of uridine which is characteristic of pyrimide biosynthesis inhibitors. The compounds of the present invention, on the other hand, while structurally similar to lefunomide, are capable of inhibiting cellular growth by a mechanism not affected by the addition of uridine. While not being bound to any particular theory, applicants believe that is is due either to fact that the heteroaryl group of the claimed compounds do not metabolize to an open form at all and therefore exhibit their activity in their native configuration, or, if they do metabolize to an open form, the chemical composition of the open form molecules to which they are converted are either inactive or active but not as inhibitors of pyrimidine biosynthesis (as evinced by the fact that uridine addition has no effect).

Thus, it appears that, while chemically similar to leflunomide, the compounds of the present invention are biologically active in an entirely different manner than leflunomide and its metabolite, A771726, and therefore comprise a new family of compounds capable of modulating protein tyrosine kinase activity.

While, again, not being bound to a particular theory, it appears that the compounds of this invention affect cell proliferation by modulating PTK signaling. The signaling related to the PTKs FGFR and PDGFR appear to be particularly susceptible to modulation by the compounds of the present invention.

As used herein, the terms "modulate", "modulation" or "modulating" refer to the alteration of the catalytic activity of PTKs. In particular, modulating refers to the activation of the catalytic activity of PTKs, more preferably the activation or inhibition of the catalytic activity of PTKs, depending on the concentration of the compound administered or, more preferably still, the inhibition of the catalytic activity of PTKs. Modulation may be effected by direct interaction with a PTK or through intervention at some other point in the biochemical process controlled by the particular PTK, the observable result of which appears as a modulation of PTK catalytic activity.

The term "catalytic activity" as used herein refers to the rate of phosphorylation of tyrosine under the influence, direct or indirect of PTKs.

A. General Structural Features

In a second aspect, the present invention relates to heteroarylcarboxamide compounds having the chemical structure shown in Formula 3:

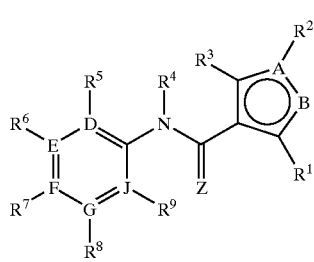

3 wherein:

A is selected from the group consisting of oxygen, nitrogen and sulfur.

B is selected from the group consisting of nitrogen and sulfur and it is understood that when B is sulfur and A is nitrogen, the nitrogen is participating in both a single bond and a double bond within the ring so that it cannot be bonded to any atom outside the ring; that is, when B is sulfur, $R^2$ cannot exist.

D, E, F, G, and J are independently selected from the group consisting of carbon and nitrogen such that the monocyclic heteroaryl six-member ring formed is one known in the chemical arts; furthermore, when D, E, F, G or J is nitrogen, $R^5$, $R^6$, $R^7$, $R^8$ or $R^9$, respectively, does not exist.

$R^1$ is selected from the group consisting of hydrogen, alkyl, cycloalkyl, alkenyl, alkynyl, aryl, heteroaryl and heteroalicyclic.

$R^2$ is selected from the group consisting of hydrogen, alkyl, cycloalkyl, alkenyl, alkynyl, aryl, heteroaryl, heteroalicyclic, carbonyl, C-carboxy, S-sulfonamido, sulfonyl, hydroxy, alkoxy, trihalomethanesulfonyl, halo, guanyl, C-amido and C-thioamido.

$R^3$ is selected from the group consisting of hydrogen, alkyl, cycloalkyl, alkenyl, alkynyl, aryl, heteroaryl and heteroalicyclic.

Z is selected from the group consisting of oxygen and sulfur.

$R^4$ is selected from the group consisting of hydrogen, alkyl, cycloalkyl, alkenyl, alkynyl, aryl heteroaryl, heteroalicyclic, sulfonyl, trihalomethanesulfonyl, hydroxy, alkoxy and C-carboxy.

$R^5$, $R^6$, $R^7$, $R^8$ and $R^9$ are independently selected from the group consisting of hydrogen, alkyl, trihaloalkyl, alkenyl, alkynyl, cycycloalkyl, aryl, heteroaryl, heteroalicyclic, hydroxy, alkoxy, cycloalkoxy, aryloxy, heteroaryloxy, heteroalicycloxy, thiohydroxy, thioalkyoxy, thiocycloalkoxy, thioheteraryloxy, thioheteralicyloxy, halo, nitro, cyano, C-O-carbamyl, N-carbamyl, O-thiocarbamyl, N-thiocarbamyl, silyl, phosphonyl, C-carboxy, O-carboxy, N-amido, C-amido, sulfinyl, sulfonyl, S-sulfonamido, N-sulfonamido, trihalomethanesulfonyl, guanyl, guanidino, trihalomethanesulfonamido, amino and —$NR^{13}R^{14}$.

$R^{13}$ and $R^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring containing at least one nitrogen.

As used herein, the term "alkyl" refers to a saturated aliphatic hydrocarbon including straight chain and branched chain groups. Preferably, the alkyl group has 1 to 20 carbon atoms (whenever a numerical range; e.g. "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$.

$R^{13}$ and $R^{14}$ are independently selected from the group consisting of hydrogen, alkyl, cycloalkyl, aryl, carbonyl, C-carboxy, sulfonyl, trihalomethysulfonyl and, combined, a five- or six-member heteroalicyclic ring containing at least one nitrogen.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituted group(s) is preferably one or more selected from alkyl, cycloalkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more selected from alkyl, cycloalkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more selected from alkyl, cycloalkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

A "hydroxy" group-refers to an —OH group.

An "alkoxyl" group refers to both an —O-alkyl and an —O-cycloalkyl group, as defined herein.

An "aryloxy" group refers to both an —O-aryl and an —O-heteroaryl group, as defined herein.

A "heteroaryloxy" group refers to a heteroaryl-O-group with heteroaryl as defined herein.

A "heteroalicycloxy" group refers to a heteroalicyclic-O-group with heteroalicyclic as defined herein.

A "thiohydroxyl" group refers to an —SH group.

A "thioalkoxyl" group refers to both an S-alkyl and an —S-cycloalkyl group, as defined herein.

A "thioaryloxy" group refers to both an —S-aryl and an —S-heteroaryl group, as defined herein.

A "thioheteroaryloxyl" group refers to a heteroaryl-S-group with heteroaryl as defined herein.

A "thioheteroalicycloxy" group refers to a heteroalicyclic-S-group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "trihalomethanecarbonyl", group refers to a $X_3$CC(=O)— group with X as defined herein.

A "C-carboxyl" group refers to a —C(=O)O—R" groups, with R" as defined herein.

An "O-carboxyl" group refers to a R"C(=O)O— group, with R" as defined herein.

A "carboxylic acid" group refers to a C-carboxyl group in which R" is hydrogen.

A "halo" group refers to fluorine, chlorine, bromine or iodine.

A "trihalomethyl" group refers to a —$CX_3$ group wherein X is a halo group as defined herein.

A "trihalomethanesulfonyl" group refers to a $X_3$CS(=O)$_2$— groups with X as defined above.

A "trihalomethanesulfonamido" group refers to a $X_3$CS(=O)$_2$$NR^{13}$— group with X and $R^{13}$ as defined herein.

A "cyano" group refers to a —C≡N group.

A "sulfinyl" group refers to a —S(=O)—R" group, with R" as defined herein.

A "sulfonyl" group refers to a —S(=O)$_2$R" group, with R" as defined herein.

An "S-sulfonamido" group refers to a —S(=O)$_2$NR$^{13}$R$^{14}$, with R$^{13}$ and R$^{14}$ as defined herein.

An "N-Sulfonamido" group refers to a R$^{13}$S(=O)$_2$NR$^{14}$— group, with R$^{13}$ and R$^{14}$ as defined herein.

An "O-carbamyl" group refers to a —OC(=O)NR$^{13}$R$^{14}$ group with R$^{13}$ and R$^{14}$ as defined herein.

An "N-carbamyl" group refers to a R$^{13}$OC(=O)NR$^{14}$ group, with R$^{13}$ and R$^{14}$ as defined herein.

An "O-thiocarbamyl" group refers to a —OC(=S)NR$^{12}$R$^{13}$ group with R$^{12}$ and R$^{13}$ as defined herein.

An "N-thiocarbamyl" group refers to a R$^{12}$OC(=S)NR$^{13}$— group, with R$^{12}$ and R$^{13}$ as defined herein.

An "amino" group refers to an —NH2 group.

A "C-amido" group refers to a —C(=O)NR$^{12}$R$^{13}$ group with R$^{12}$ and R$^{13}$ as defined herein.

An "N-amido" group refers to a R$^{12}$C(=O)NR$^{13}$— group, with R$^{12}$ and R$^{13}$ as defined herein.

A "C-thioamido" group refers to a —C(=S)NR$^{12}$R$^{13}$ group with R$^{12}$ and R$^{13}$ and defined herein.

A "ureido" group refers to a —NR$^{12}$C(=O)NR$^{13}$R$^{14}$ group, with R$^{12}$ and R$^{13}$ as defined herein and R$^{14}$ defined the same as R$^{12}$ and R$^{13}$.

A "guanidino" group refers to a —R$^{12}$NC(=N)NR$^{13}$R$^{14}$ group, with R$^{12}$, R$^{13}$ and R$^{14}$ as defined herein.

A "guanyl" group refers to a R$^{12}$R$^{13}$NC(=N)—' group, with R$^{12}$ and R$^{13}$ as defined herein.

A "nitro" group refers to a —NO$_2$ group.

A "cyano" group refers to a —C≡N group.

A "silyl" group refers to a —Si(R")$_3$, with R" as defined herein.

A "methylenedioxy" group refers to a —OCH$_2$O— group where the two oxygens are covalently bonded to two adjacent carbon atoms of an aryl or heteroaryl ring with aryl and heteroaryl as defined herein.

A "1,3-dioxano" group refers to a —CH$_2$OCH$_2$O— group where the —CH$_2$ and the oxygen are covalently bonded to two adjacent carbon atoms of an aryl or heteroaryl ring with aryl and heteroaryl as defined herein.

Examples of monocyclic heteroaryl six-member rings known in the chemical arts include, but are not limited to, the following:

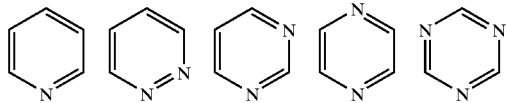

B. Preferred Structural Features

Preferred structural features for the claimed compounds are those in which:

A is oxygen and B is nitrogen;

R$^1$ is selected from the group consisting of hydrogen, alkyl, cycloalkyl, alkenyl and alkynyl; and, R$^3$ is selected from the group consisting of hydrogen, alkyl, cycloalkyl and aryl; and, R$^4$ is hydrogen.

Further preferred structures for the claimed compounds are those in which:

A and B are nitrogen;

R$^2$ is selected from the group consisting of hydrogen, alkyl and cycloalkyl;

Z is oxygen;

R$^5$, R$^8$ and R$^9$ are hydrogen;

R$^6$ is selected from the group consisting or hydrogen and alkyl; and,

R$^7$ is selected from the group consisting of hydrogen, trihalomethyl and trihalomethanesulfonyl Other preferred embodiments of the present invention are those in which:

R$^6$ and R$^7$ combined, form a methylenedioxy or a 1,3-dioxano group.

And, finally, a preferred structure for the claimed compounds is that in which J is nitrogen.

2. THE BIOCHEMISTRY

In yet another embodiment, this invention relates to a method for the treatment or prevention of a disorder characterized by inappropriate PTK activity comprising administering to a patient inflicted with such a disorder a therapeutically effective amount of one or more of the disclosed compounds or a physiologically acceptable salt thereof.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmacological, biological, biochemical and medical arts.

As used herein, the terms "prevent", "preventing" and "prevention" refer to a method for barring an organism from in the first place acquiring an PTK mediated cellular disorder.

As used herein, the terms "treat", "treating" and "treatment" refer to a method of alleviating or abrogating a PTK mediated cellular disorder and/or its attendant symptoms. With regard particularly to cancer, these terms simply mean that the life expectancy or an individual affected with a cancer will be increased or that one or more of the symptoms of the disease will be reduced.

As used herein, the term "cancer" refers to various types of malignant neoplasms, most of which can invade surrounding tissues, and may metastasize to different sites, as defined by Stedman's Medical Dictionary 25th edition (Hensyl ed. 1990). Examples of cancers which may be treated by the present invention include, but are not limited to, brain, ovarian, colon, prostate, kidney, bladder, breast, lung, oral and skin cancers which exhibit inappropriate PTK activity. These types of cancers can be further characterized. For example, brain cancers include glioblastoma multiforme, anaplastic astrocytoma, astrocytoma, ependymoma, oligodendroglioma, medulloblastoma, meningioma, sarcoma, hemangioblastoma, and pineal parenchymal. Skin cancers include melanoma and Kaposi's sarcoma.

A "disorder characterized by inappropriate PTK activity" includes, but is not limited to, cell proliferative disorders, cell differentiation disorders, cell growth disorders and metastatic disorders. Such disorders include, but are not limited to, cancer, as described above and, in addition, the development of neoplasia such as carcinoma, sarcoma, leukemia, glioblastoma and hemangioma as well as disorders such as psoriasis, arteriosclerosis, arthritis and diabetic retinopathy (and other disorders related to uncontrolled angiogenesis and/or vasculogenesis), fibrotic disorders and metabolic disorders.

Unwanted cell proliferation can result from inappropriate. PTK activity occurring in different types of cells including cancer cells, cells surrounding a cancer cell (stromal cells), endothelial cells and smooth muscle cells. For example, and without limitation, an increase in FGFR and/or PDGFR activity of endothelial cells surrounding cancer cells may lead to an increased vascularization (angiogenesis) of a tumor, thereby facilitating growth of the cancer cells. Inappropriate PTK activity may also contribute to the proliferation of cancer cells by direct mitogenic stimulation.

"Cell proliferative disorders" refer to disorders wherein unwanted cell proliferation of one or more subset of cells in a multicellular organism occurs resulting in harm (e.g., discomfort or decreased life expectancy) to the multicellular organism. Cell proliferative disorders can occur in different types of animals and in humans. Cell proliferative disorders include cancers, skeletal disorders, angiogenic or blood vessel proliferative disorders, fibrotic disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., 1993, *Kidney International* 43:47S–54S.

Other examples of cell proliferative disorders are disclosed in the following references which are incorporated as if fully set forth herein. EGFRs (Tuzi et al., 1991, *Br. J. Cancer* 63:227–233; Torp et al., 1992, *APMIS* 100:713–719) HER2/neu (Slamon et al., 1989, *Science* 244:707–712) and the PDGF-R (Kumabe et al., 1992, *Oncogene*, 7:627–633) are over-expressed in many tumors and/or persistently activated by autocrine loops. In fact, in the most common and severe cancers, these receptor over-expressions (Akbasak and Suner-Akbasak et al., 1992, *J. Neurol. Sci.*, 111:119–133; Dickson et al., 1992, *Cancer Treatment Res.* 61:249–273; Korc et al., 1992, *J. Clin. Invest.* 90:1352–1360) and autocrine loops (Lee and Donoghue, 1992, *J. Cell. Biol.*, 118:1057–1070; Korc et al., supra; Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma, lung, ovarian, melanoma and prostate. The RTK c-met has been generally associated with hepatocarcinogenesis and thus hepatocellular carcinoma. Additionally, c-met has been linked to malignant tumor formation. More specifically, the RTK c-met has been associated with, among other cancers, colorectal, thyroid, pancreatic and gastric carcinoma, leukemia and lymphoma. Additionally, over-expression of the c-met gene has been detected in patients with Hodgkins disease, Burkitts disease, and the lymphoma cell line.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.*, 50:2511–2517). In addition, IGF-I, integrally involved in the normal growth and differentiation of the nervous system, appears to be an autocrine stimulator of human gliomas. Sandberg-Nordqvist et al., 1993, *Cancer Res.* 53:2475–2478. The importance of the IGF-IR and its ligands in cell proliferation is further supported by the fact that many cell types in culture (fibroblasts, epithelial cells, smooth muscle cells, T-lymphocytes, myeloid cells, chondrocytes and osteoblasts, the stem cells of the bone marrow) are stimulated to grow by IGF-I. Goldring and Goldring, 1991, *Eukarvotic Gene Expression*, 1:301–326. In a series of recent publications, Baserga even suggests that IGF-IR plays a central role in the mechanisms of transformation and, as such, could be a preferred target for therapeutic interventions for a broad spectrum of human malignancies. Baserga, 1995, *Cancer Res.*, 55:249–252; Baserga, 1994, *Cell* 79:927–930; Coppola et al., 1994, *Mol. Cell. Biol.*, 14:4588–4595.

The term "organism" refers to any living entity comprised of at least one cell. A living organism can be as simple as, for example, a single eukariotic cell or as complex as a mammal, including a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor; (2) inhibiting (that is, slowing to some extent, preferably stopping) tumor metastasis; (3) inhibiting to some extent (that is slowing to some extent, preferably stopping) tumor growth; and/or, (4) relieving to some extent (or preferably eliminating) one or more symptoms associated with the cancer.

A "therapeutically effective amount", in reference to the treatment of a cell proliferative disorder other than a cancer refers to an amount sufficient to bring about one or more of the following results: inhibit the growth of cells causing the disorder, relieve discomfort due to the disorder, or prolong the life of a patient suffering from the disorder.

The association between abnormal PTK activity and disease are not restricted to cancer. For example, RTKs have been associated with metabolic diseases like psoriasis, diabetes mellitus, wound healing, inflammation, and neurodegenerative diseases. For example, EGFR involvment has been indicated in corneal and dermal wound healing.

Defects in the Insulin-R and the IGF-IR are indicated in type-II diabetes mellitus. A more complete correlation between specific RTKs and their therapeutic indications is set forth in Plowman et al., *DN&P* 7:334–339 (1994).

As noted previously, not only RTKs but CTKs as well including, but not limited to, src, abl, fps, yes, fyn, lyn, lck, blk, hck, fgr and yrk (reviewed by Bolen et al., *FASEB J.*, 6:3403–3409 (1992)) are involved in the proliferative and metabolic signal transduction pathway and thus were expected, and have been shown, to be involved in many PTK-mediated disorders to which the present invention is directed. For example, mutated src (v-src) has been demonstrated to be an oncoprotein (pp60$^{v\text{-}src}$) in chicken. Moreover, its cellular homolog, the proto-oncogene pp60$^{c\text{-}src}$ transmits the oncogenic signals of many receptors. For example, over-expression of EGFR or HER2/neu in tumors leads to the constitutive activation of pp60$^{c\text{-}src}$, which is characteristic of the malignant cell but absent in the normal cell. On the other hand, mice deficient in the expression of c-src exhibit an osteopetrotic phenotype, indicating a key participation of c-src in osteoclast function and a possible involvement in related disorders. Similarly, Zap70 is implicated in T-cell signaling.

In particular, the compounds of the present invention are expected to be useful in the treatment and prevention of cell proliferative disorders characterized by inappropriate activity of an FGFR, PDGFR or related receptors.

i. FGFR, PDGFR and Related Receptors.

As discussed above, the FGFR family contains at least four distinct members: FGFR1 (also called Flg and Cek1), FGFR2 (also called Bek, Ksam, KsamI and Cek3), FGFR3 (also called Cek2) and FGFR4. They share a common structure consisting of, in the mature protein, one or more immunoglobulin-like (IgG-like) loops flanked by characteristic cysteines, a hydrophobic transmembrane domain and a intracellular domain containing a catalytic region that is split by a short insert. (See Ullrich and Schlessinger, *Cell* 61:203, 1990.) The degree of homology varies between them, with the highest homology being found in the catalytic domain. Additional diversity in the family is created through splice variants that vary the number and character of the IgG-like regions in the extracellular domain. At least nine FGFR ligands have been identified including FGF1 (acidic FGF), FGF2 (basic FGF), FGF3 (int-2), FGF4 (Kaposi FGF), FGF5, FGF6, FGF7 (keratinocyte growth factor (KGF)), FGF8 (androgen-induced growth factor) and FGF9. Multiple members of the FGF ligand family can bind to the same receptor species. For a general review of FGFs and FGFRs see Johnson and Williams, *Adv. in Cancer Res.* 60:1, 1993.

The PDGF receptor family, on the other hand, contains only the two isoforms PDGFR-alpha and PDGFR-beta, which are known to heterodimerize. PDGF ligand is a pleiotropic factor that exists as a homo- or heterodimer of two polypeptides, the A- and B-chains (Habenicht, et al., *Klin. Wochen-Schrift* 68:53, 1990; Heldin, *EMBO J.* 11:4251, 1992). Other tyrosine kinase receptors structurally and functionally related to FGFR and PDGFR include Flt (de Vries, et al., *Science* 255:989, 1992) and KDR (Terman, et al., *BBRC* 187;1579, 1992), both of which are activated by the ligand VEGF (Rosenthal, et al., *Growth Factors*, 4:53–59, 1990; Conn, et al., *Proc. Natl. Acad. Sci. (USA)*, 87:1323–1327, 1990; Houck, et al., *Mol. Endocrinol.*, 5:1806–1814, 1991). VEGF expression is known to be increased by hypoxia (such as would be found in growing tumors) and is known to stimulate endothelial cells and to be involved in angiogenesis (Plate et al., *Nature*, 359:845–848, 1992; Shweike, et al., *Nature* 359:843–845, 1992).

PDGFR- and FGF-dependent signaling is initiated immediately following binding of ligand to a receptor. Ligand binding induces receptor dimerization, either homodimers or heterodimers, leading to activation of receptor tyrosine kinase activity and autophosphorylation. Activation of the receptor leads to increased tyrosine phosphorylation on a number of cellular proteins, although many of their identities and functions are still largely unknown. Depending on the cell type, PDGFR and/or FGFR activation ultimately leads to proliferation, differentiation, inhibition of differentiation, motility, etc.

The use of the present invention is facilitated by first determining whether a disorder is related to inappropriate PDGFR and/or FGFR activity. Once such disorders are identified, patients suffering from such a disorder can be identified by analysis of their symptoms by procedures well known to medical doctors. Such patients can then be treated as described herein.

Many well known techniques exist for determining whether a disorder is related to inappropriate PDGFR and/or FGFR activity. For example, comparisons can be made in the level of expression of FGF and/or PDGF ligand or FGFR and/or PDGFR in a tumor biopsy with levels in similar normal tissues or tumor cells known to be unrelated to FGFR and/or PDGFR activity (such as A431 cells, Yaish, et al., *Science* 242:933, 1988). Such comparisons can be done by immunostaining with FGFR and/or PDGFR specific antibodies or binding and detecting FGF and/or PDGF ligand using techniques well known in the art, by Northern blot analysis for the presence of ligand or receptor RNA, or by transcript imaging (Plowman, WO96/34985, published Nov. 7, 1996, and incorporated by reference herein). Alternatively, samples can be analyzed for level of receptor phosphorylation, which is indicative of activity, compared to normal tissues. Receptor phosphorylation is readily detected by means well known in the art such as by using anti-phosphotyrosine antibodies. If the cancer cells have a higher level of FGFR and/or PDGFR activity or expression than non-FGFR and/or PDGFR driven cancers or normal tissues, also preferably a level equal to or greater than previously identified FGFR and/or PDGFR driven cancers, then the cancer cells are candidates for treatment using the compounds discussed herein.

In the case of cell proliferative disorders arising from to unwanted proliferation of non-cancer cells, the level of receptor activity is compared to that level occurring in the general population (e.g., the average level occurring in the general population of people or animals excluding those people or animals suffering from a cell proliferative disorder). If the unwanted cell proliferation disorder is characterized by a higher receptor level than that occurring in the general population, then the disorder is a candidate for treatment using the compounds described herein.

ii. FGFR- and PDGFR-Related Disorders

One class of PTK disorders which involves FGFR and/or PDGFR is the cell proliferative disorders. As discussed above, proliferative disorders result in unwanted cell proliferation of one or more subset of cells in a multicellular organism resulting in harm to the organism. Two ways in which inappropriate PTK/FGFR/PDGFR activity can stimulate unwanted cell proliferation of a particular type of cell are by directly stimulating growth of the particular cell or by increasing vascularization of a particular area (angiogenesis), such as tumor tissue, thereby facilitating growth of the tissue. Angibgenesis also plays a significant role in metastasis, a complex disorder which is discussed in more detail below.

Cell proliferative disorders include cancers, blood vessel proliferation disorders, skeletal malformations and fibrotic disorders. These disorders are not necessarily independent. For example, fibrotic disorders may be related to, or overlap with, blood vessel disorders. For example, Moyamoya disease (which is characterized herein as a blood vessel disorder) results in the abnormal formation of fibrous tissue in the intracranial arteries.

Not all cancers found in a particular location within the body will be treatable by the method of the invention, only those characterized by inappropriate FGFR, PDGFR or related receptor activity. For example, only 30% of bladder carcinomas are characterized as highly invasive and prone to metastasis (Raghavan, et al., *NEJM* 322:1129, 1990; Allen and Maher, *J. Cell. Physiol.* 155:368, 1993), and these have been associated with FGFR activity (Allen and Maher, supra). Breast cancers are associated with inappropriate FGFR activity in 12%–32% of cases (Adnane, et al., *Oncogene* 6:659, 1991; Penault-Llorca, et al., *Int. J. Cancer* 61:170, 1995). Friess, et al., (*Chirug* 65:604, 1994) report that approximately 50% of primary pancreatic cancers surveyed express FGFR, and this expression was associated with tumor aggressiveness as measured by significantly shorter post-operative survival. Holm, et al. (*Int. J. Oncology* 9:1077, 1996) found expression of PDGFR in only 30% of non-small cell lung cancer cell lines examined, and only 10% expressed KDR. Seymour, et al. (supra) found expression of PDGF in 43% of tumors from breast cancer patients. Expression of PDGF correlated with a reduced chance of survival. One can determine which cancers are treatable by the compounds and methods of the invention by employing the techniques described above for determining inappropriate FGFR and/or PDGFR activity.

The formation and spreading of blood vessels, or vasculogenesis and angiogenesis respectively, play important roles in a variety of physiological processes such as embryonic development, wound healing and organ regeneration. They also play a role in cancer development. Blood vessel proliferation disorders refer to angiogenic and vasculogenic disorders generally resulting in abnormal proliferation of blood vessels. Examples of such disorders, besides cancer, include Moyamoya disease and macular degeneration. FGFR and KDR have been recognized has having a regulatory role in angiogensis, along with other factors, due to their role in both endothelial cell proliferation and migration (Friesel and Maciag, *FASEB J.* 9:919, 1995; Folkman and Klagsbrun, *Science* 235:442, 1987; Mullins and Rifkin, *J. Cell. Physiol.* 119:247, 1984; Gualandris, et al., *Cell Growth & Diff.* 7:147, 1996). FGFR activity has been suggested to play a role specifically in the angiogenesis associated with macular degeneration (Amin, et al., *Invest. Ophthal. and Vis. Sci.* 35(8):3178, 1994). PDGF and VEGF expression is associated with angiogeneis and metastasis in breast cancer (Anan, et al., *Surgery* 119:333, 1996). PDGF expression has been correlated with increased blood vessel count in colon cancers (Hsu, et al., *J. Cell. Physiol.* 165:239, 1995). PDGF and FGF have been shown to induce secretion of VEGF by glioma cells (Tsai, et al., *J. Neurosurg.* 82:864, 1995).

Moyamoya disease is characterized by intracranial carotid artery stenosis and occlusions and a fine network of vessels at the base of the brain; it thus may be described as both an angiogenic and fibrotic disorder (Suzuki and Kodama, Stroke 14:104, 1983; Suzuki and Takaku, *Arch. Neurol.* 20:288, 1969). Suzui, et al., (*Neurosurgery* 35(1):20, 1994) have found that both FGF ligand and FGFR are increased in the superficial temporal artery of patients with Moyamoya disease.

Fibrotic disorders refer to the abnormal formation of extracellular matrix. Examples of fibrotic disorders include those found in the liver (hepatic cirrhosis), kidney (glomerular sclerosis, interstitial nephritis), lung (interstitial pulmonary fibrosis), arteries (restenosis, atherosclerosis) and skin (wound scarring, scleroderma).

Hepatic cirrhosis is characterized by an increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Inappropriate FGFR activity can stimulate lipocyte proliferation.

As noted above, other proliferative disorders involving FGFR, PDGFR and other PTKs can be identified by standard techniques, as well as by determination of the efficacy of action of the compound described herein.

iii. Metastatic Disorders

Liotta, et al. describe invasion and metastasis as "the most life-threatening aspects of the oncogenic process" (See review in Liotta, et al., *Cell* 64:327, 1991). Invasion and metastasis are F-2 complex events mediated by a group of coordinated cellular processes. They are facilitated by proteins that stimulate tumor cell attachment to an extracellular matrix, proteolysis of barriers such as the basement membrane, migration into the circulatory system and attachment to and colony formation in distant organs. There is also a significant correlation between metastatic potential and angiogeneic potential, and the two processes may have many factors in common. (See Claffey, et al., *Cancer Res.* 56:172, 1996; Takahashi, et al., *Cancer Res.* 55:3964, 1995.)

The cellular responses induced by FGF, PDGF and VEGF ligands include those necessary for metastasis: proliferation, migration, production of proteases, and nebvascularization. FGFR and PDGFR expression have been associated with increased aggressiveness and metastasis of a number of cancers. Nakamoto, et al. (*Cancer Research* 52:571, 1992) compared FGF and FGFR expression and responsiveness in several human prostate cancer cell lines. The degree of metastasis in murine models shown by each of the cell lines (LNCaP, DU145 and PC3) correlated directly with FGFR expression (with LNCaP being the lowest and PC3 being the highest), although the biological consequences of FGFR expression were not studied in depth. Allen and Maher, *J. Cell. Phys.* 155:368, 1993) report a similar study with bladder carcinoma cell lines. In a comparison of invasive and non-invasive tumors the invasive tumor (EJ) showed a significant increase in FGFR at both the protein and RNA level, with the non-invasive tumor, (RT4) showing almost no FGFR present. The FGFR was also shown to be biologically active by receptor phosphorylation in response to ligand. Anan, et al. (supra) found PDGF mRNA was expressed more frequently in breast tumors with lymph node metastases that in those without metastases.

In addition to all of the above, both RTKs and CTKs are currently suspected as being involved in hyperimmune disorders.

This invention is therefore directed to compounds which modulate PTK signal transduction by affecting the enzymatic activity of the PTKs and thereby interfering with the signal transduced by such proteins. More particularly, the present invention is directed to compounds which modulate the PTK-mediated signal transduction pathways as a therapeutic approach to cure many kinds of solid tumors, including but not limited to carcinoma; sarcoma, leukemia, erythroblastoma, glioblastoma, meningioma, astrocytoma, melanoma and myoblastoma. Indications may include, but are not limited to, brain cancers, bladder cancers, ovarian cancers, gastric cancers, pancreas cancers, colon cancers, blood cancers, lung cancers, bone cancers and leukemias.

The term "administering" as used herein refers to a method for introducing a compound of this invention into a milieu containing a PTK, including both in vitro, i.e. in a test tube, and in vivo, i.e. into cells or tissues of a living organism, milieus. Thus, the PTK mediated disorders which are the object of this invention can be studied, prevented or treated by the methods set forth herein whether the cells or tissues of the organism exist within the organism or outside the organism. Cells existing outside the organism can be maintained or grown in cell culture dishes. In this context, the ability of a particular compound to affect a PTK related disorder; i.e., the IC50 of the compound, defined below, can be determined before the use of the compounds in more complex living organisms is attempted. For cells outside the organism, multiple methods exist, and are well-known to those skilled in the arts, to administer compounds including, but not limited to, cell micro-injection, transformation and numerous carrier techniques. For cells harbored within a living organism, myriad methods also exist, and are likewise well-known to those skilled in the art, to administer compounds including, but not limited to, oral, parenteral, dermal, injection and aerosol applications.

As used herein, "PTK related disorder," "PTK driven disorder", "abnormal PTK activity" and "inappropriate PTK activity" all refer to a disorder characterized by inappropriate activity or over-activity of PTKs, which can be either RTKs or CTKs. Inappropriate activity refers to either: (1) PTK expression in cells which normally do not express PTKs; (2) increased PTK expression leading to unwanted cell proliferation, differentiation and/or growth; or, (3) decreased PTK expression leading to unwanted reductions in cell proliferation, differentiation and/or growth. Overactivity of PTKs refers to either amplification of the gene encoding a particular PTK or production of a level of PTK activity which can correlate with a cell proliferation, differentiation and/or growth disorder (that is, as the level of the PTK increases, the severity of one or more of the symptoms of the cellular disorder increases).

The methods and compositions of the invention are designed to inhibit unwanted cell proliferation or metastasis by altering the activity of PTKs. Without being bound to any theory, inhibition of the activity of PTKs may occur by inhibiting tyrosine phosphorylation of a RTK, by inhibiting substrate or adaptor protein binding to the receptor, or by inhibiting other downstream signaling events, thereby inhibiting the activity of the RTK. However, unless otherwise stated, the use of the claimed methods and compositions are not limited to this particular theory.

C. Pharmacological Compositions and Therapeutic Applications

The compounds disclosed herein are preferably administered to a patient in a pharmaceutical composition comprising one or more compounds of this invention together with pharmaceutically acceptable carrier(s) and/or excipients. The compounds can be prepared as a physiologically acceptable salts (i.e., non-toxic salts which do not prevent the compound from exerting its effect).

Physiologically acceptable salts can be acid addition salts such as hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. These salts can be derived using acids such as hydrochloric acid, sulfuric acid, phosphoric acid and sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Physiologically acceptable salts can be prepared by standard techniques. For example, the free base form of the compound is first dissolved in a suitable solvent such as water or a water-alcohol solution containing the appropriate acid. The salt is then isolated by evaporating the solution. In a another example, the salt is prepared by reacting the free base and acid in an organic solvent.

Carriers or excipient can be used to facilitate administration of the compound, for example, to increase the solubility of the compound. Examples of carriers and excipient include calcium carbonate, calcium phosphate, various sugars or types of starch, cellulose derivatives, gelatin, vegetable oils, polyethylene glycols and physiologically compatible solvents. The compositions or pharmaceutical composition can be administered by different routes including intravenously, intraperitoneally, subcutaneously, intramuscularly, orally, topically, or transmuccosally.

The specific delivery route of any selected agent depends on the use of the agent. Generally, a specific delivery program for each agent focuses on agent uptake with regard to intracellular localization, followed by demonstration of efficacy. Alternatively, delivery to these same cells in an organ or tissue of an animal can be pursued. Uptake studies include uptake assays to evaluate, e.g., cellular nucleic acid or protein uptake, regardless of the delivery vehicle or strategy. Such assays also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity not only includes cell viability but also cell function. Generally, the dosages of the mutated protein and nucleic acid is as described above for the featured compounds.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles increase the circulation half-life of drugs which would otherwise be rapidly cleared from the blood stream. Some examples of such specialized drug delivery vehicles falling into this category are liposomes, hydrogels, cyclodextrins, biodegradable nanocapsules, and bioadhesive microspheres. Pumps can also be used for this purpose.

From this category of delivery systems, liposomes are the preferred approach. Liposomes increase intracellular stability, increase uptake efficiency and improve biological activity. Liposomes are hollow spherical vesicles composed of lipids arranged in a similar fashion to those lipids making up the cell membrane. They have an internal aqueous space for entrapping water soluble compounds and range in size from 0.05 to several microns in diameter. Antibodies can be attached to liposomes to target particular cells.

Topical administration of the featured compound is advantageous, particularly when treating skin disorders such as Kaposi's sarcoma, since it allows localized concentration at the site of administration with minimal systemic adsorption. This simplifies the delivery strategy of the agent to the disease site and reduces the extent of toxicological characterization. Furthermore, the amount of material applied is far less than that required for other administration routes.

Many compounds are preferably absorbed systemically when used to treat disorders such as cancer. Systemic absorption refers to the accumulation of drugs in the blood stream followed by distribution throughout the entire body. Administration routes which lead to systemic absorption include: intravenous, subcutaneous, intraperitonreal, intranasal and intrathecal. Each of these administration routes expose the drug to an accessible diseased tissue. Subcutaneous administration drains into a localized lymph node and proceeds through the lymphatic network into the circulatory system. The rate of entry into the circulatory system has been shown to be a function of molecular weight or size.

Some of the compounds of this invention may be hydrophobic and thus not very soluble in water. Effective doses of hydrophobic compounds for systemic administration can be obtained using the pharmaceutical formulations described in U.S. Pat. No. 5,610,173, issued Mar. 11, 1997. A particularly preferred formulation is obtained using a combination of the compound and VPD:D5W. VPD consists of a solution of 12% w/v polysorbate 80, 0.55% citric acid (anhydrous), 35% w/v polyenthlene glycol (MW=300 daltons) and 26.3% v/v 190 proof ethanol. VPD is diluted 1:22 in a diluent. Preferred diluents are 0.45% saline, and 0.9% saline. A particularly preferred diluent is 5% dextrose in water (D5W).

Another way of overcoming the hydrophobicity problem includes the use of frequent small daily doses rather than a few large daily doses. For example, the composition can be administered at short time intervals, preferably the composition can be administered using a pump to control the time interval or achieve continuously administration. Suitable pumps are commercially available (e.g., the ALZET® pump sold by Alza corporation, and the BARD ambulatory PCA pump sold by Bard MedSystems).

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropyl-methylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in an admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The proper dosage depends on various factors such as the type of disease being treated, the particular composition being used, the dosing regimen and the size and physiological condition of the patient. For the treatment of cancers it is prefered that the minimal plasma concentration in a patient be greater than 5 μg/ml, more preferably greater than 25 μg/ml, most preferably greater than 50 μg/ml. The compound can be delivered daily or less frequently provided plasma levels of the active moiety are sufficient to maintain therapeutic effectiveness. Plasma levels may be reduced if pharmacological effective concentrations of the drug are achieved at the site of interest.

Toxicity and therapeutic efficacy of such compounds can be determined by standard pharmaceutical procedures in cell cultures or experimental animals; that is the $LD_{50}$ (the dose lethal to 50% of the population) and the $ED_{50}$ (the dose therapeutically effective in 50% of the population) can be determined. The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

4. SYNTHESIS

The compounds of this invention may be readily synthesized using techniques well known in the chemical arts. The following syntheses are shown by way of example only and are not to be construed as limiting in any way. In fact, it will be appreciated by those skilled in the art that other synthetic pathways for forming the compounds of the invention are available and that the following are but a few of the possible routes to the claimed compounds.

a. 3-Methyl-4-[4-(trifluoromethyl)phenyl-aminocarbonyl]isoxazole.

Ethyl propiolate (2.8 g) and pyrrolidine (1.4 g) in 5 mL of acetonitrile are mixed at room temperature for 1 hour, the solvent evaporated and the ethyl 3-pyrrolidin-1-acrylate used as isolated or distilled under vacuum. Triethylamine (0.25 mL) is added to a mixture of 1.8 g of ethyl 3-pyrrolidin-1-acrylate, 0.9 g of nitroethane and 2.5 g of phenyl isothiocyanate in 10 mL of toluene at room temperature and stirred overnight. The mixture is then refluxed for 0.5 hour, cooled, and the diphenylurea removed by filtration. The mixture is washed with water and brine, dried over anhydrous sodium sulfate, and evaporated to dryness under vacuum to give 1.4 g of ethyl 3-methyl-4-isoxazolecarboxylate. (Stork, G., McMurry, J. C., *J. Am. Chem. Soc.* 89, 5461,1967).

Ethyl 3-methyl-4-isoxazolecarboxylate (1.3 g) is stirred at room temperature overnight in 5 mL of ethanol and 10 mL of 2.5 N sodium hydroxide. Dilution with water, cooling in ice, and acidification to pH 2 with 6 N hydrochloric acid precipitates an off-white solid which is collected by vacuum filtration, washed with ethanol/water, and dried under vacuum to give 1.0 g of 3-methyl-4-isoxazolecarboxylic acid.

3-Methyl-4-isoxazolecarboxylic acid (0.9 g) is stirred with 5 mL of thionyl chloride at room temperature for one hour and the mixture evaporated to dryness. The residue is dissolved in 5 mL 3 tetrahydrofuran and 1 mL of pyridine containing 1.2 g of 4-trifluoromethylaniline and stirred overnight. The mixture is refluxed for one hour, cooled and diluted with water to give an off-white precipitate. The solid is collected by vacuum filtation, washed with ethanol/water and dried under vacuum to give 1.2 g of 3-methyl-4-[4-(trifluoromethyl)phenylamino-carbonyl]isoxazole.

b. 3-Methyl-4-[4-(trifluoromethyl)phenylaminocarbonyl]isoxazole.

A solution of 5.5 g of 4-(trifluoromethyl)aniline in 6-mL of toluene at 120° C. is treated with 5.4 g of 2,2,6-trimethyl-4H-1,3-dioxin-4-one. The mixture is refluxed for four hours and cooled. The precipitate is collected by vacuum filtration, washed with toluene and dried to give 6 g of N-[4-(trifluoromethyl)phenylacetoacetamide.

N-[4-(Trifluoromethyl)phenylacetoacetamide (6 9), 4 g of triethylorthoformate and 8 g of acetic anhydride is cautiously heated to reflux for 2 hours. The reaction is cooled to room temperature and the precipitate collected by vacuum filtration and dried to give 4 g of N-[4-(trifluoromethyl)phenyl]-2-(ethoxymethylene)acetoacetamide.

N-[4-(Trifluoromethyl)phenyl]-2-(ethoxymethylene)acetoacetamide (4 g) is suspended in 10 mL of ethanol treated with 1.5 g of hydroxylamine hydrochloride in 10 mL of water which has been adjusted to pH 5 with sodium hydroxide. The mixture is stirred and warmed to 40° C. for 2 hours, then cooled to room temperature and the precipitate collected by vacuum filtration. Sodium hydroxide (1 g) is added to the filtrate which is stirred for 30 minutes. The mixture is acidified to pH 2 with 6 N hydrochloric acid and the precipitate collected by vacuum filtration. The filtrate is then diluted with 100 mL of water and allowed to stand at 4° C. overnight. The precipitate is collected by vacuum filtration, washed with ethanol:water 2:1 and dried to give 300 mg of crude 3-methyl-4-[4-(trifluoromethyl)-phenylaminocarbonyl]isoxazole. The crude is purified on a column of silica gel eluting with ethyl acetate:hexane 1:4 to give 100 mg of 3-methyl-4-[4-(trifluoromethyl)phenylaminocarbonyl]-isoxazole, an off-white solid.

c. 3-Methyl-4-[4-(trifluoromethyl)phenylaminocarbonyl]-pyrazole.

N-[4-(Trifluoromethyl)phenyl]-2-(ethoxymethylene)-acetoacetamide (1 g) in 3 mL of ethanol is stirred overnight with 0.3 g of hydrazine hydrate. The precipitate is collected by vacuum filtration, washed with ethanol:water 2:1 and dried to give 0.3 g of 3-methyl-4-(4-(trifluoromethyl)phenylaminocarbonyl]pyrazole as an off-white solid.

d. 3-Methyl-4-(pyrid-2-aminocarbonyl)isoxazole.

By substituting 2-aminopyridine for 4-(trifluoromethyl)aniline in a, the identical process gives 1 g of 3-methyl-4-(pyrid-2-aminocarbonyl)isoxazole as an off-white solid.

e. 3-Methyl-4-(pyrid-2-aminocarbonyl)pyrazole.

By substituting 2-aminopyridine for 4-(trifluoromethyl)aniline in the first two steps of the process of b, the identical process gives 2.5 g of N-(pyrid-2-yl)-2-(ethoxymethylene)-acetoacetamide. By substituting N-(pyrid-2-yl)-2-(ethoxymethylene)acetoacetamide for N-(4-(trifluoromethyl)phenyl]-2-ethoxymethylene)acetoacetamide in c, the identical process gives 0.3 g of 3-methyl-4-(pyrid-2-aminocarbonyl)pyrazole as an off-white solid.

f. 3-Cyclopropyl-4-[4-(trifluoromethyl)phenylaminocarbonyl]isoxazole.

By substituting cyclopropylnitromethane (Williams et al (1965) *J. Org. Chem.* 30: 2674–2675) for nitroethane in a, the identical process gives 1.2 g of 3-cyclopropyl-4-[4-(trifluoromethyl)phenylaminocarbonyl]-isoxazole as an off white solid.

g. 3-Cyclopropyl-4-[4-(trifluoromethyl)phenylaminocarbonyl]pyrazole.

Methyl cyclopropylcarbonylacetate (1.4 g) and 1.6 g of 4-(trifluoromethyl)aniline are heated to 160° C. overnight. When the crude product (or the product purified by crystallization or silica gel chromatography) is substituted for N-[4-trifluoro-methylphenyl]acetoacetamide in the-second step of b, the identical process gives N-[4-trifluoromethyl phenyl]-2-(ethoxy-methylene) cyclopropylcarbonylacetamide. When N-[4-trifluoromethylphenyl]-2-(ethoxymethylene)cyclopropylcarbonyl-acetamide is substituted for N-[4-(trifluoromethyl)-phenyl]-2-(ethoxy-methylene)-acetoacetamide in c, the identical process gives 3-cyclopropyl-4-[4-(trifluoromethyl)phenylaminocarbonyl]-pyrazole.

h. 3-Cyclopropyl-4-(pyrid-2-aminocarbonyl)isoxazole.

When 2-aminopyridine is substituted for 4-(trifluoromethyl )aniline in f, the identical process gives 3-cyclopropyl-4-(pyrid-2-aminocarbonyl) isoxazole.

i. 3-Cyclopropyl-4-(pyrid-2-aminocarbonyl)pyrazole.

When 2-aminopyridine is substituted for 4-(trifluoromethyl)aniline in g, the identical process gives 3-cyclopropyl-4-(pyrid-2-aminocarbonyl)pyrazole.

j. 3-Methyl-4-[3-methyl-4-(trifluoromethyl)phenylaminocarbonyl]isoxazole;

3-Methyl-4-[4-(trifluoromethylsulfonyl)phenylaminocarbonyl]isoxazole.

By substituting 3-methyl-4(trifluoromethyl)aniline (Tordeaux, M., et al (1990) *J. Chem. Soc. Perkin Trans. EN* 8: 2293–2299) and 4-(trifluoromethylsulfonyl)aniline (Jagupolski, M. (1954) *Zh. Obshch. Khim.* 24: 887–893, *Engl. Ausg. S.* 885–889)for 4-(trifluoromethyl)aniline in the identical process of a, 3-methyl-4-[3-methyl-4-(trifluoromethyl)-phenylaminocarbonyl]-isoxazole and 4-[4-(trifluoromethylsulfonyl)phenylaminocarbonyl]-isoxazole are prepared.

k. 3-Methyl-4-[3-methyl-4-(trifluoromethyl) phenylaminocarbonyl]pyrazole;

3-Methyl-4-[4-(trifluoromethylsulfonyl) phenylaminocarbonyl]pyrazole.

By substituting the appropriate amine for 4-(trifluoromethyl)aniline in the identical process of g, 3-methyl-4-[3-methyl-4-(trifluoromethyl)phenylaminocarbonyl]-pyrazole and 3-Methyl-4-[4-(trifluoromethylsulfonyl) phenylaminocarbonyl]pyrazole are prepared.

l. 3-Allyl-4-[4-(trifluoromethyl)phenylaminocarbonyl]-isoxazole;

3-Allyl-4-(pyrid-2-aminocarbonyl)isoxazole;

3-Allyl-4-[3-methyl-4-(trifluoromethyl) phenylaminocarbonyl]isoxazole;

3-Allyl-4-[4-(trifluoromethylsulfonyl) phenylaminocarbonyl]isoxazole.

By substituting 4-nitro-1-butene (Seebach, D., et al (1978) *Angew. Chem. GE* 90: 479–480) for nitroethane in a, and then the appropriate amines for 4-(trifluoromethyl)-aniline in a, the identical process gives 3-allyl-4-[4-(trifluoromethyl)phenylaminocarbonyl]isoxazole, 3-allyl-4-(pyrid-2-aminocarbonyl)-isoxazole, 3-allyl-4-[3-methyl-4-(trifluoromethyl)phenylaminocarbonyl]isoxazole and 3-allyl-4-[4-(trifluoromethylsulfonyl)-phenylaminocarbonyl]isoxazole.

m. 3-Allyl-4-[4-(trifluoromethyl)phenylaminocarbonyl] pyrazole;

3-Allyl-4-(pyrid-2-aminocarbonyl)pyrazole;

3-Allyl-4-[3-methyl-4-(trifluoromethyl) phenylaminocarbonyl]pyrazole;

3-Allyl-4-[4-(trifluoromethylsulfonyl) phenylaminocarbonyl]pyrazole.

By substituting methyl 3-butenoate for methyl cyclbpropylcarbonylacetate in g, and then the appropriate amines for 4-(trifluoromethyl)aniline in g, the identical process gives 3-allyl-4-([4-(trifluoromethyl)phenylamino-carbonyl] pyrazole, 3-allyl-4-(pyrid-2-aminocarbonyl)pyrazole), 3-allyl-4-[3-methyl-4-(trifluoromethyl)phenyl-aminocarbonyl]pyrazole, and 3-allyl-4-[4-(trifluoromethylsulfonyl) phenylaminocarbonyl]-pyrazole.

n. 3, 5-Dimethyl-4-[E4-(trifluoromethyl) phenylaminocarbonyl]isoxazole;

3,5-Dimethyl-4-(pyrid-2-aminocarbonyl) isoxazole;

3,5-Dimethyl-4-[(3-methyl-4-(trifluoromethyl) phenylaminocarbonyl]isoxazole;

3,5-Dimethyl-4-[4-(trifluoromethylsulfonyl) phenylaminocarbonyl]isoxazole.

By using 3,5-dimethyl-4-chlorocarbonylisoxazole or by substituting ethyl methylpropiolate for ethyl propiolate in a and then the appropriate amines for 4-(trifluoromethyl) aniline in a, the identical process gives 3,5-dimethyl-4-[4-(trifluoromethyl) phenylaminocarbonyl]isoxazole, 3,5-dimethyl-4-(pyrid-2-aminocarbonyl)isoxazole, 3,5-dimethyl-4-[3-methyl-4-(trifluoromethyl)-phenylaminocarbonyl]isoxazole (Example 25), and 3,5-dimethyl-4-[4-(trifluoromethylsulfonyl) phenylaminocarbonyl]isoxazole.

o. 3,5-Dimethyl-4-[4-(trifluoromethyl) phenylaminocarbonyl]pyrazole;

3,5-Dimethyl-4-(pyrid-2-aminocarbonyl)isoxazole; 3,5-Dimethyl-4-(pyrid-2-aminocarbonyl)pyrazole;

3,5-Dimethyl-4-[3-methyl-4-(trifluoromethyl) phenylaminocarbonyl]pyrazole;

3,5-Dimethyl-4-[4-(trifluoromethylsulfonyl) phenylaminocarbonyl]pyrazole.

By substituting triethylorthoacetate for triethylorthoformate in the second step of b, and then substituting the appropriate amines for 4-(trifluoromethyl) aniline in b, the identical process gives the corresponding substituted 2-(ethoxymethylene)acetoacetamides. By substituting the corresponding substituted 2-(ethoxymethylene) acetoacetamides for N-[4-(trifluoromethyl)phenyl]-2-(ethoxymethylene)acetoacetamide in c, the identical process gives 3,5-dimethyl-4-[4-(trifluoromethyl) phenylaminocarbonyl]pyrazole, 3,5-dimethyl-4-(pyrid-2-aminocarbonyl)pyrazole, 3,5-dimethyl-4-[3-methyl-4-(trifluoromethyl)phenylaminocarbonyl]pyrazole, and 3,5-dimethyl-4-[4-(trifluoromethyl-sulfonyl) phenylaminocarbonyl]pyrazole.

p. 5-(2-Chlorophenyl)-3-methyl-4-[4-(trifluoromethyl)-phenylaminocarbonyl]isoxazole;

p. 5-(2-chlorophenyl)-3-methyl-4-(pyrid-2-aminocarbonyl)-isoxazole;

5-(2-chlorophenyl)-3-methyl-4-[3-methyl-4-(trifluoromethyl)phenylaminocarbonyl]isoxazole;

5-(2-Chlorophenyl)-3-methyl-4-[4-(trifluoromethylsulfonyl)phenylaminocarbonyl]isoxazole.

By substituting ethyl 2-chlorophenylpropiolate (Newman, M. (1955) *J. Amer. Chem. Soc.* 77:5549) for ethyl propiolate in a, and then the appropriate amines for 4-(trifluoromethyl) aniline in a, the identical process gives 5-(2-chlorophenyl)-3-methyl-4-[4-(trifluoromethyl)phenylamino-carbonyl] isoxazole, 5-(2-chlorophenyl)-3-methyl-4-(pyrid-2-aminocarbonyl)isoxazole, 5-(2-chlorophenyl)-3-methyl-4-[3-methyl-4-(trifluoromethyl)phenylaminocarbonyl] isoxazole, 5-(2-chlorophenyl)-3-methyl-4-[4-(trifluoromethylsulfonyl)phenylaminocarbonyl]isoxazole.

q. 5-(2-Chlorophenyl)-3-methyl-4-[4-(trifluoromethyl)-phenylaminocarbonyl]pyrazole;

5-(2-chlorophenyl)-3-methyl-4-(pyrid-2-aminocarbonyl) pyrazole;

5-(2-chlorophenyl)-3-methyl-4-[3-methyl-4-(trifluoromethyl)phenylaminocarbonyl]pyrazole;

5-(2-Chlorophenyl)-3-methyl-4-[4-(trifluoromethylsulfonyl)phenylaminocarbonyl]pyrazole.

By substituting methyl 2-chlorobenzoylacetate for methylcyclopropylcarbonylacetate in g, and then substituting the appropriate amines for 4-(trifluoromethyl)aniline in g, the identical process with triethylorthoacetate substituted for triethylorthoformate in b, gives 5-(2-chlorophenyl)-3-methyl-4-[4-(trifluoromethyl)-phenylaminocarbonyl] pyrazole, 5-(2-chlorophenyl)-3-methyl-4-(pyrid-2-aminocarbonyl)pyrazole, 5-(2-chlorophenyl)-3-methyl-4-[3-methyl-4-(trifluoromethyl)-phenylaminocarbonyl] pyrazole and 5-(2-chlorophenyl)-3-methyl-4-[4-(trifluoromethylsulfonyl) phenylaminocarbonyl]pyrazole.

r. 5-(2-Chlorophenyl)-3-cyclopropyl-4-[4-(trifluoromethyl) phenylaminocarbonyl]isoxazole;

5-(2-Chlorophenyl)-3-cyclopropyl-4-(pyrid-2-minocarbonyl)isoxazole; 5-(2-Chlorophenyl)-3-cyclopropyl-4-[3-methyl-4-(trifluoromethyl) phenylaminocarbonyl]isoxazole; 5-(2-chlorophenyl)-3-cyclopropyl-4-[4-(trifluoromethyl-sulfonyl) phenylaminocarbonyl]isoxazole.

By substituting ethyl 2-chlorophenylpropiolate for ethyl propiolate and cyclopropylnitromethane for nitroethane in a, and then the appropriate amines for 4-(trifluoromethyl) aniline in a, the identical process gives 5-(2-chlorophenyl)-3-cyclopropyl-4-[4-(trifluoromethyl) phenylaminocarbonyl] isoxazole, 5-(2-chlorophenyl)-3-cyclopropyl-4-(pyrid-2-aminocarbonyl)-isoxazole, and 5-(2-chlorophenyl)-3- cyclopropyl-4-[3-methyl-4-(trifluoromethyl)phenylaminocarbonyl]isoxazole and 5-(2-chlorophenyl)-3-cyclopropyl-4-[4-(trifluoromethylsulfonyl)-phenylaminocarbonyl]isoxazole.

s. 5-(2-Chlorophenyl)-3-cyclopropyl-4-[4-(trifluoromethyl)phenylaminocarbonyl]-pyrazole;

5-(2-chlorophenyl)-3-cyclopropyl-4-(pyrid-2-aminocarbonyl)pyrazole;

5-(2-Chlorophenyl)-3-cyclopropyl-4-[3-methyl-4-(trifluoromethyl)phenylaminocarbonyl]pyrazole;

5-(2-chlorophenyl)-3-cyclopropyl-4-[4-(trifluoromethylsulfonyl)phenylaminocarbonyl]pyrazole.

By substituting the appropriate amines for 4-(trifluoromethyl)aniline in a, and then by substituting triethyl-2-chloroorthobenzoate for triethylorthoformate in b, the identical process of a gives 5-(2-chlorophenyl)-3-cyclopropyl-4-[4-(trifluoromethyl) phenylaminocarbonyl]pyrazole, 5-(2-chlorophenyl)-3-cyclopropyl-4-(pyrid-2-aminocarbonyl)pyrazole, and 5-(2-chlorophenyl)-3-cyclopropyl-4-[3-methyl-4-(trifluoromethyl)phenylaminocarbonyl]pyrazole and 5-(2-chlorophenyl)-3-cyclopropyl-4-[3-methyl-4-(trifluoromethyl-sulfonyl)phenylaminocarbonyl]pyrazole.

t. 3-(2-Carboxyethyl)-4-[4-(trifluoromethyl)phenylaminocarbonyl]isoxazole;

3-(2-carboxy-ethyl)-4-(pyrid-2-aminocarbonyl)isoxazole;

3-(2-Carboxyethyl)-4-[3-methyl-4-(trifluoromethyl)-phenylaminocarbonyl]isoxazole;

3-(2-Carboxyethyl)-[4-(trifluoromethylsulfonyl)phenylaminocarbonyl]isoxazole.

By substituting ethyl 4-(t-butoxycarbonylethyl) nitrobutane (from 4-nitrobutyric acid methyl ester, Bissell, E. R. et al., *Tetrahedron* (1970), p 5737–5743) for ethyl propiolate in a, and then the appropriate amines for 4-(trifluoromethyl)aniline in a, the identical process followed by removal of the t-butyl group gives 3-(2-carboxyethyl)-4-[4-(trifluoromethyl)phenylaminocarbonyl]isoxazole, 3-(2-carboxyethyl)-4-(pyrid-2-aminocarbonyl)-isoxazole, 3-(2-carboxyethyl)-4-[3-methyl-4-(trifluoromethyl)-phenylaminocarbonyl]isoxazole, and 3-(2-carboxyethyl)-[4-(trifluoromethylsulfonyl)phenylaminocarbonyl]isoxazole u. 3-(2-Carboxyethyl)-4-[4-(trifluoromethyl)phenylaminocarbonyl]pyrazole;

3-(2-carboxyethyl)-4-(pyrid-2-aminocarbonyl)pyrazole;

3-(2-Carboxyethyl)-4-[3-methyl-4-(trifluoromethyl)phenyl-aminocarbonyl]pyrazole;

3-(2-carboxyethyl)-[4-(trifluoromethylsulfonyl)phenylaminocarbonyl]pyrazole.

By substituting ethyl 2-(t-butoxycarbonyl)priopionoacetate for ethyl cyclopropylcarbonylacetate in g, and then substituting the appropriate amines for 4-(trifluoromethyl)aniline in g, the identical process, followed by removal of the t-butyl group, gives 3-(2-carboxy-ethyl)-4-[4-(trifluoromethyl)phenylaminocarbonyl]pyrazole, 3-(2-carboxyethyl)-4-(pyrid-2-aminocarbonyl)-pyrazole, 3-(2-carboxyethyl)-4-[3-methyl-4-(trifluoromethyl)-phenylaminocarbonyl]pyrazole, and 3-(2-carboxyethyl)-[4-(trifluoromethylsulfonyl)-phenylaminocarbonyl]pyrazole.

v. 4-(1,3-Benzodioxan-6-aminocarbonyl)-3-methylisoxazole;

4-(1,3-Benzodioxan-6-aminocarbonyl)-3-cyclopropylisoxazole;

4-(1,3-Benzodioxan-6-aminocarbonyl)-3,5-dimethylisoxazole;

4-(1,3-Benzodioxan-6-aminocarbonyl)-3-cyclopropyl-5-methylisoxazole;

4-(1,3-benzodioxan-6-aminocarbonyl)-5-(2-chlorophenyl)-3-methylisoxazole;

4-(1,3-Benzodioxan-6-aminocarbonyl)-5-(2-chlorophenyl)-3-cyclopropylisoxazole.

By substituting 6-amino-1,3-benzodioxane for 4-(trifluoromethyl)aniline in a, and then substituting the appropriate substituted priopiolates for methyl priopiolate and/or the appropriate substituted nitromethanes for nitroethane in a, the identical process gives 4-(1,3-benzodioxan-6-aminocarbonyl)-3-methylisoxazole, 4-(1,3-benzo-dioxan-6-aminocarbonyl)-3-cyclopropylisoxazole, 4-(1,3-benzodioxan-6-aminocarbonyl)-3,5-dimethylisoxazole, 4-(1,3-benzodioxan-6-aminocarbonyl)-3-cyclopropyl-5-methylisoxazole, 4-(1,3-benzodioxan-6-aminocarbonyl)-5-(2-chlorophenyl)-3-methylisoxazole, and 4-(1,3-benzodioxan-6-aminocarbonyl)-5-(2-chlorophenyl)-3-cyclopropylisoxazole.

w. 4-(1,3-Benzodioxan-6-aminocarbonyl)-3-methylpyrazole;

4-(1, 3-Benzodioxan-6-aminocarbonyl)-3-cyclopropylpyrazole;

4-(1,3-Benzodioxan-6-amrinocarbonyl)-3,5-dimethylpyrazole;

4-(1,3-Benzodioxan-6-aminocarbonyl)-3-cyclopropyl-5-methylpyrazole;

4-(1,3-Benzodioxan-6-aminocarbonyl)-5-(2-chlorophenyl)-3-methylpyrazole;

4-(1,3-Benzodioxan-6-aminocarbonyl)-5-(2-chlorophenyl)-3-cyclopropylpyrazole.

By substituting 6-amino-1,3-benzodioxane for 4-(trifluoromethyl)aniline in g, and then the appropriate substituted acetoacetate for methyl cyclopropylcarbonyl-acetoacetate and/or the appropriate substituted orthoester for triethylorthoformate in the second step of b, the identical process of the second step of b and of g gives 4-(1,3-benzodioxan-6-aminocarbonyl)-3-methylpyrazole, 4-(1,3-benzodioxan-6-aminocarbonyl)-3-cyclopropylpyrazole, 4-(1,3-benzodioxan-6-aminocarbonyl)-3,5-dimethylpyrazole, 4-(1,3-benzodioxan-6-aminocarbonyl)-3-cyclopropyl-5-methylpyrazole, 4-(1,3-benzodioxan-6-aminocarbonyl)-5-(2-chlorophenyl)-3-methylpyrazole, and 4-(1,3-benzodioxan-6-aminocarbonyl)-5-(2-chlorophenyl)-3-cyclopropylpyrazole.

x. 4-(1,3-Benzodioxol-5-aminocarbonyl)-3-methylisoxazole;

4-(1,3-Benzodioxol-5-aminocarbonyl)-3-cyclopropylisoxazole;

4-(1,3-Benzodioxol-5-aminocarbonyl)-3,5-dimnethylisoxazole;

4-(1,3-Benzodioxol-5-aminocarbonyl)-3-cyclopropyl-5-methylisoxazole;

4-(1,3-Benzodioxol-5-aminocarbonyl)-5-(2-chlorophenyl)-3-methylisoxazole;

4-(1,3-benzo-dioxol-5-aminocarbonyl)-5-(2-chlorophenyl)-3-cyclopropylisoxazole.

By substituting 5-amino-1,3-benzodioxole for 4-(trifluoromethyl)aniline in a, and then substituting the appropriate substituted propiolic ester for ethyl propiolate and/or the appropriate stubstituted nitromethane for nitroethane in a, the identical process gives 4-(1,3-benzodioxol-5-aminocarbonyl)-3-methylisoxazole, 4-(1,3-benzodioxol-5-aminocarbonyl)-3-cyclopropylisoxazole, 4-(1,3-benzodioxol-5-aminocarbonyl])-3,5-dimethylisoxazole, 4-(1,3-benzodioxol-5-aminocarbonyl)-3-cyclopropyl-5- methylisoxazole, and 4-(1,3-benzodioxol-5-aminocarbonyl)-5-(2-chlorophenyl)-3-methylisoxazole, and 4-(1,3-benzodioxol-5-aminocarbonyl)-5-(2-chlorophenyl)-3-cyclopropylisoxazole.

y. 4-(1,3-Benzodioxol-5-aminocarbonyl)-3-methylpyrazole;

4-(1,3-Benzodioxol-5-amino-carbonyl)-3-cyclopropylpyrazole;

4-(1,3-Benzodioxol-5-aminocarbonyl])-3,5-dimethylpyrazole;

4-(1,3-Benzodioxol-5-aminocarbonyl)-3-cyclopropyl-5-methylpyrazole;

4-(1,3-Benzodioxol-5-aminocarbonyl)-5-(2-chlorophenyl)-3-methylpyrazole;

4-(1,3-Benzodioxol-5-aminocarbonyl)-5-(2-chlorophenyl)-3-cyclopropylpyrazole.

By substituting 5-amino-1,3-benzodioxole for 4-(trifluoromethyl)aniline in g, and then substituting the appropriate substituted acetoacetate for ethyl cyclopropylcarbonylacetate and/or the appropriate substituted orthoformate for triethylorthoformate in the second step of b, the identical process of the second step of b and of g gives 4-(1,3-benzodioxol-5-aminocarbonyl)-3-methylpyrazole, 4-(1,3-benzodioxol-5-aminocarbonyl)-3-cyclopropylpyrazole, 4-(1,3-benzodioxol-5-aminocarbonyl])-3,5-dimethylpyrazole, 4-(1,3-benzodioxol-5-aminocarbonyl)-3-cyclopropyl-5-methylpyrazole, 4-(1,3-benzodioxol-5-aminocarbonyl)-5-(2-chlorophenyl)-3-methylpyrazole, and 4-(1,3-benzodioxol-5-aminocarbonyl)-5-(2-chlorophenyl)-3-cyclopropylpyrazole.

z. 3-Methyl-4-[4-(trifluoro-methyl)phenylaminocarbonyl]thiazole;

3-Methyl-4-(pyrid-2-aminocarbonyl)thiazole;

3-Methyl-4-[3-methyl-4-trifluoromethyl)phenylaminocarbonyl]thiazole;

3-Methyl-4-[4-(trifluoromethylsulfonyl)phenylaminocarbonyl]thiazole.

By substituting 3-methyl-4-thiazole carboxylic acid (Buttimore, D. et al.; *J. Chem. Soc.* (1963) p 2032–2039) for 3-methyl-4-isoxazole carboxylic acid in a, and then substituting the appropriate amines for 4-(trifluoromethyl) aniline in a, the identical process gives 3-methyl-4-[4-(trifluoromethyl)phenylaminocarbonyl]thiazole, 3-methyl-4-(pyrid-2-aminocarbonyl)-thiazole, 3-methyl-4-[3-methyl-4-(trifluoromethyl) phenylamino-carbonyl]thiazole, and 3-methyl-4-[4-(trifluoromethylsulfonyl) phenylaminocarbonyl]thiazole.

5. BRIEF DESCRIPTION OF THE TABLES

Table 1 is a comparison of the activity of leflunomide, its metabolite and a compound of this invention as inhibitor of FGF induced DNA synthesis alone or with added uridine.

Table 2 shows the results of the ability of several of the compounds of this invention to inhibit DNA synthesis induced by FGF, PDGF and EGF.

Table 3 shows the results of a subcutaneous xenograft experiment testing the ability of Cmpd. 1 to inhibit tumor growth in vivo and, in addition, testing the toxic effects of Cmpd. 1 at the dose used.

6. BIOLOGICAL EVALUATION

It will be appreciated that, in any given series of compounds, a spectrum of biological activity will be afforded. In its most preferred embodiments, this invention relates to novel heteroarylcarboxamides demonstrating the ability to modulate PTK activity. The following assays are employed to select those compounds demonstrating the optimal degree of the desired activity.

As used herein, the phrase "optimal degree of the desired activity" refers to the lowest IC50, defined elsewhere herein, against a PTK related to a particular disorder so as to provide an organism, preferably a human, with a therapeutically effective amount of a compound of this invention at the lowest possible dosage.

The following in vitro assays may be used to determine the level of activity and effect of the different compounds of the present invention on one or more of the RTKs. Similar assays can be designed along the same lines for any PTK using techniques well known in the art.

The cellular/catalytic assays described herein are performed in an ELISA format. The general procedure is a follows: a compound is introduced to cells expressing the test kinase, either naturally or recombinantly, for some period of time after which, if the test kinase is a receptor, a ligand known to activate the receptor's activity is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The cellular/biologic assays described herein measure the amount of DNA made in response to activation of a test kinase, which is a general measure of a proliferative response. The general procedure for this assay is as follows: a compound is introduced to cells expressing the test kinase, either naturally or recombinantly, for some period of time after which, if the test kinase is a receptor, a ligand known to activate the receptor's activity is added. After incubation at least overnight, a DNA labeling reagent such as Bromodeoxy-uridine (BrdU) or 3H-thymidine is added. The amount of labeled DNA is detected with either an anti-BrdU antibody or by measuring radioactivity and is compared to control cells not contacted with a test compound.

1. Cellular/Catalytic Assays

Enzyme linked immunosorbent assays (ELISA) may be used to detect and measure the presence of PTK activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. Of Microbiology, Washington, D.C.

The disclosed protocol may be adapted for determining activity with respect to a specific RTK. For example, the preferred protocols for conducting the ELISA experiments for specific RTKs is provided below. Adaptation of these protocols for determining a compound's activity for other members of the RTK family, as well as for CTKs, is well within the scope of knowledge of those skilled in the art.

a. FLK-1

An ELISA assay can be conducted to measure the kinase activity of the FLK-1 receptor and more specifically, the inhibition or activation of TK activity on the FLK-1 receptor. Specifically, the following assay can be conducted to measure kinase activity of the FLK-1 receptor in cells genetically engineered to express Flk-1.

Materials and Methods

Materials. The following reagents and supplies are being used:

a. Corning 96-well ELISA plates (Corning Catalog No. 25805-96);
b. Cappel goat anti-rabbit IgG (catalog no. 55641);
c. PBS (Gibco Catalog No. 450-1300EB);
d. TBSW Buffer (50 mM Tris (pH 7.2), 150 mM NaCl and 0.1% Tween-20);
e. Ethanolamine stock (10% ethanolamine (pH 7.0), stored at 4° C.)
f. HNTG buffer (20 mM HEPES buffer (pH 7.5), 150 mM NaCl, 0.2% Triton X-100, and 10% glycerol);
g. EDTA (0.5 M (pH 7.0) as a 100×stock);
h. Sodium ortho vanadate (0.5 M as a 100×stock);
i. Sodium pyro phosphate (0.2M as a 100× stock);
j. NUNC 96 well V bottom polypropylene plates (Applied Scientific Catalog No. AS-72092);
k. NIH3T3 C7#3 Cells (FLK-1 expressing cells)
l. DMEM with 1× high glucose L Glutamine (catalog No. 11965–050);
m. FBS, Gibco (catalog no. 16000-028);
n. L-glutamine, Gibco (catalog no. 25030-016);
o. VEGF, PeproTech, Inc. (catalog no. 100-20) (kept as 1 $\mu$g/100 $\mu$l stock in Milli-Q d$H_2$O and stored at −20° C.;
p. Affinity purified anti-FLK-1 antiserum;
q. UB40 monoclonal antibody specific for phosphotyrosine (see, Fendley, et al., 1990, *Cancer Research* 50:1550–1558);
r. EIA grade Goat anti-mouse IgG-POD (BioRad catalog no. 172-1011);
s. 2,2-azino-bis(3-ethylbenz-thiazoline-6-sulfonic acid (ABTS) solution (100 mM citric acid (anhydrous), 250 mM $Na_2HPO_4$ (pH 4.0), 0.5 mg/ml ABTS (Sigma catalog no. A-1888)), solution should be stored in dark at 4° C. until ready for use;
t. $H_2O_2$ (30% solution) (Fisher catalog no. H325);
u. ABTS/$H_2O_2$ (15 ml ABTS solution, 2 $\mu$l $H_2O_2$) prepared 5 minutes before use and left at room temperature;
v. 0.2 M HCl stock in $H_2O$;
w. dimethylsulfoxide (100%) (Sigma Catalog No. D-8418); and
y. Trypsin-EDTA (Gibco BRL Catalog No. 25200-049).

Protocol. The following protocol is being used for conducting the assay:

1. Coat Corning 96-well elisa plates with 1.0 $\mu$g per well Cappel Anti-rabbit IgG antibody in 0.1M $Na_2CO_3$ pH 9.6. Bring final volume to 150 $\mu$l per well. Coat plates overnight at 4° C. Plates can be kept up to two weeks when stored at 4° C.
2. Grow cells in Growth media(DMEM, supplemental with 2.0 mM L-Glutamine, 106 FBS) in suitable culture dishes until confluent at 37° C., 5% $CO_2$.
3. Harvest cells by trypsinization and seed in Corning 25850 polystyrene 96-well roundbottom cell plates, 25.000 cells/well in 200 $\mu$l of growth media.
4. Grow cells at least one day at 37° C., 5% $CO_2$.
5. Wash cells with D-PBS 1×.
6. Add 200 $\mu$l/well of starvation media (DMEM, 2.0 mM 1-Glutamine, 0.1% FBS). Incubate overnight at 37° C., 5% $CO_2$.
7. Dilute Compounds 1:20 in polypropylene 96 well plates using starvation media. Dilute dimethylsulfoxide 1:20 for use in control wells.
8. Remove starvation media from 96 well cell culture plates and add 162 $\mu$l of fresh starvation media to each well.
9. Add 18 $\mu$l of 1:20 diluted Compound dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% $CO_2$ for two hours.
10. Remove unbound antibody from ELISA plates by inverting plate to remove liquid. Wash 3 times with TBSW+ 0.5% ethanolamine, pH 7.0. Pat the plate on a paper towel to remove excess liquid and bubbles.
11. Block plates with TBSW+0.5% Ethanolamine, pH 7.0, 150 $\mu$l per well. Incubate plate thirty minutes while shaking on a microtiter plate shaker.
12. Wash plate 3 times as described in step 10.
13. Add 0.5 $\mu$g/well affinity purified anti-FLU-1 polyclonal rabbit antiserum. Bring final volume to 150 $\mu$l/well with TBSW+0.5% ethanolamine pH 7.0. Incubate plate for thirty minutes while shaking.
14. Add 180 $\mu$l starvation medium to the cells and stimulate cells with 20 $\mu$l/well 10.0 mM sodium ortho vanadate and 500 ng/ml VEGF (resulting in a final concentration of 1.0 mM sodium orthovanadate and 50 ng/ml VEGF per well) for eight minutes at 37° C., 5% $CO_2$. Negative control wells receive only starvation medium.
15. After eight minutes, media should be removed from the cells and washed one time with 200 $\mu$l/well PBS.
16. Lyse cells in 150 $\mu$l/well HNTG while shaking at room temperature for five minutes. HNTG formulation includes sodium ortho vanadate, sodium pyro phosphate and EDTA.
17. Wash ELISA plate three times as described in step 10.
18. Transfer cell lysates from the cell plate to elisa plate and incubate while shaking for two hours. To transfer cell lysate pipette up and down while scrapping the wells.
19. Wash plate three times as described in step 10.
20. Incubate ELISA plate with 0.02 kg/well UB40 in TBSW+05% ethanolamine. Bring final volume to 150 $\mu$l/well. Incubate while shaking for 30 minutes.
21. Wash plate three times as described in step 10.
22. Incubate ELISA plate with 1:10,000 diluted EIA grade goat anti-mouse IgG conjugated horseradish peroxidase in TBSW+0.5% ethanolamine, pH 7.0. Bring final volume to 150 $\mu$l/well. Incubate while shaking for thirty minutes.
23. Wash plate as described in step 10.
24. Add 100 $\mu$l of ABTS/$H_2O_2$ solution to well. Incubate ten minutes while shaking.
25. Add 100 $\mu$l of 0.2 M HCl for 0.1 M HCl final to stop the color development reaction. Shake 1 minute at room temperature. Remove bubbles with slow stream of air and read the ELISA plate in an ELISA plate reader at 410 nm.

b. HER-2 ELISA

Assay 1: EGF-Receptor-HER2 Chimeric Receptor Assay In Whole Cells.

HER2 kinase activity in whole EGFR-NIH3T3 cells are measured as described below:

Materials and Reagents. The following materials and reagents are being used to conduct the assay:

a. EGF: stock concentration=16.5 ILM; EGF 201, TOYOBO, Co., Ltd. Japan.
b. 05-101 (UBI) (a monoclonal antibody recognizing an EGFR extracellular domain).
c. Anti-phosphotyrosine antibody (anti-Ptyr) (polyclonal) (see, Fendley, et al., supra).
d. Detection antibody: Goat anti-rabbit lgG horse radish peroxidase conjugate, TAGO, Inc., Burlingame, Calif.

e. TBST buffer:

| | |
|---|---|
| Tris-HCl, pH 7.2 | 50 mM |
| NaCl | 150 mM |
| Triton X-100 | 0.1 | f. HNTG 5×stock:

| | |
|---|---|
| HEPES | 0.1M |
| NaCl | 0.75M |
| Glycerol | 50% |
| Triton X-100 | 1.0% | g. ABTS stock:

| | |
|---|---|
| Citric Acid | 100 mM |
| $Na_2HPO_4$ | 250 mM |
| HCl, conc. | 0.5 pM |
| ABTS* | 0.5 mg/ml |

*(2,2-azinobis(3-ethyibenzthiazolinesuifonic acid)). Keep solution in dark at 4° C. until use.

h. Stock reagents of:
EDTA 100 mM pH 7.0
$Na_3VO_4$ 0.5 M
$Na_4(P_2O_7)$ 0.2 M

Procedure. The following protocol is being used:

A. Pre-coat ELISA Plate

1. Coat ELISA plates (Corning, 96 well, Cat. #25805–96) with 05–101 antibody at 0.5 g per well in PBS, 100 μl final volume/well, and store overnight at 4° C. Coated plates are good for up to 10 days when stored at 4° C.

2. On day of use, remove coating buffer and replace with 100 μl blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

B. Seeding Cells

1. An NIH3T3 cell line overexpressing a chimeric receptor containing the EGFR extracellular domain and intracellular HER2 kinase domain can be used for this assay.

2. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.

3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μl per well, in a 96 well microtiter plate. Incubate seeded cells in 5% $CO_2$ at 37° C. for about 40 hours.

C. Assay Procedures

1. Check seeded cells for contamination using an inverted microscope. Dilute drug stock (10 mg/ml in DMSO) 1:10 in DMEM medium, then transfer 5 1 to a TBST well for a final drug dilution of 1:200 and a final DMSO concentration of 1%. Control wells receive DMSO alone. Incubate in 5% $CO_2$ at 37° C. for two hours.

2. Prepare EGF ligand: dilute stock EGF in DMEM so that upon transfer of 10 μl dilute EGF (1:12 dilution), 100 nM final concentration is attained.

3. Prepare fresh HNTG* sufficient for 100 μl per well; and place on ice.

| HNTG* (10 ml): | |
|---|---|
| HNTG stock | 2.0 ml |
| milli-Q $H_2O$ | 7.3 ml |
| EDTA, 100 mM, pH 7.0 | 0.5 ml |
| $Na_3VO_4$, 0.5M | 0.1 ml |
| $Na_4(P_2O_7)$, 0.2M | 0.1 ml |

4. After 120 minutes incubation with drug, add prepared SGF ligand to-cells, 10 μl per well, to a final concentration of 100 nM. Control wells receive DMEM alone. Incubate, shaking, at room temperature, for 5 minutes.

5. Remove drug, EGF, and DMEM. Wash cells twice with PBS. Transfer HNTG to cells, 100 μl per well. Place on ice for 5 minutes. Meanwhile, remove blocking buffer from other ELISA plate and wash with TBST as described above.

6. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

7. Remove lysate and wash 4 times with TBST. Transfer freshly diluted anti-Ptyr antibody to ELISA plate at 100 μl per well. Incubate shaking at room temperature for 30 minutes in the presence of the anti-Ptyr-antiserum (1:3000 dilution in TBST).

8. Remove the anti-Ptyr antibody and wash 4 times with TBST. Transfer the freshly diluted TAGO anti-rabbit IgG antibody to the ELISA plate at 100 μl per well. Incubate shaking at room temperature for 30 minutes (anti-rabbit IgG antibody: 1:3000 dilution in TBST).

9. Remove TAGO detection antibody and wash 4 times with TBST. Transfer freshly prepared $ABTS/H_2O_2$ solution to ELISA plate, 100 μl per well. Incubate) shaking at room temperature for 20 minutes. ($ABTS/H_2O_2$ solution: 1.0 μl 30% $H_2O_2$ in 10 ml ABTS stock).

10. Stop reaction by adding 50 μl 5N $H_2SO_4$ (optional), and determine O.D. at 410 nm.

11. The maximal phosphotyrosine signal is determined by subtracting the value of the negative controls from the positive controls. The percent inhibition of phosphotyrosine content for extract-containing wells is then calculated, after subtraction of the negative controls.

c. PDGF-R ELISA

All cell culture media, glutamine, and fetal bovine serum can be purchased from Gibco Life Technologies (Grand Island, N.Y.) unless otherwise specified. All, cells are grown in a humid atmosphere of 90–95% air and 5–10% $CO_2$ at 37° C. All cell lines are routinely subcultured twice a week and are negative for mycoplasma as determined by the Mycotect method (Gibco).

For ELISA assays, cells (U1242, obtained from Joseph Schlessinger, NYU) are grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium, cells are changed to serum-free medium and treated with test compound for 2 hr in a 5% $CO_2$, 37° C. incubator. Cells are then stimulated with ligand for 5–10 minute followed by lysis with HNTG (20 mM Hepes, 150 mM NaCl, 10% glycerol, 5 mM EDTA, 5 mM $Na_3VO_4$, 0.2% Triton X-100, and 2 mM NaPyr). Cell lysates (0.5 mg/well in PBS) are transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates are incubated with shaking for 1 hour at room temperature. The plates are washed with TBST four times and then incubated with polyclonal anti-phosphotyrosine antibody at room temperature for 30 minutes. Excess anti-phosphotyrosine antibody was removed by rinsing the plate with TBST four times. Goat anti-rabbit IgG antibody was added to the ELISA plate for 30 min at room temperature followed by rinsing with TBST four more times. ABTS (100 mM citric acid, 250 mM $Na_2HPO_4$ and 0.5 mg/mL 2,2'-azino-bis(3-ethylbenzthiazoline-6-sulfonic acid)) plus $H_2O_2$ (1.2 mL 30% $H_2O_2$ to 10 ml ABTS) was added to the ELISA plates to start color development. Absorbance at 410 nm with a reference wavelength of 630 nm was recorded about 15 to 30 min after ABTS addition.

d. IGF-I RECEPTOR ELISA

The following protocol may be used to measure phosphotyrosine level on IGF-I receptor, which indicates IGF-I receptor tyrosine kinase activity.

Materials And Reagents. The following materials and reagents are used:

a. The cell line used in this assay is 3T3/IGF-1R, a cell line genetically engineered to overexpresses IGF-1 receptor.

b. NIH3T3/IGF-1R is grown in an incubator with 5% $CO_2$ at 37° C. The growth media is DMEM+10% FBS (heat inactivated)+2 mM L-glutamine.

c. Affinity purified anti-IGF-1R antibody 17–69.

d. D-PBS:

| | |
|---|---|
| $KH_2PO_4$ | 0.20 g/l |
| $K_2HPO_4$ | 2.16 g/l |
| KCl | 0.20 g/l |
| NaCl | 8.00 g/l (pH 7.2) | e. Blocking Buffer: TBST plus 5% Milk (Carnation Instant Non-Fat Dry Milk).

f. TBST buffer:

| | |
|---|---|
| Tris-HCl | 50 mM |
| NaCl | 150 mM (pH 7.2/HCl 10N) |
| Triton X-100 | 0.1% |

Stock solution of TBS (10×) is prepared, and Triton X-100 is added to the buffer during dilution.

g. HNTG buffer:

| | |
|---|---|
| HEPES | 20 mM |
| NaCl | 150 mM (pH 7.2/HCl 1N) |
| Glycerol | 10% |
| Triton X-100 | 0.2% |

Stock solution (5×) is prepared and kept at 4° C.

h. EDTA/HCl: 0.5 M pH 7.0 (NaOH) as 100×stock.

i. $Na_3VO_4$: 0.5 M as 100×stock and aliquots are kept in −80° C.

j. $Na_4P_2O_7$: 0.2 M as 100×stock.

k. Insulin-like growth factor-1 from Promega (Cat #G5111).

l. Rabbit polyclonal anti-phosphotyrosine antiserum.

m. Goat anti-rabbit IgG, POD conjugate.(detection antibody), Tago (Cat. No. 4520, Lot No. 1802): Tago, Inc., Burlingame, Calif.

n. ABTS (2.2'-azinobis(3-ethylbenzthiazolinesulfonicacid))solution:

| | |
|---|---|
| Citric acid | 100 mM |
| $Na_2HPO_4$ | 250 mM (pH 4.0/1N HCl) |
| ABTS | 0.5 mg/ml | o. Hydrogen Peroxide: 30% solution is kept in the dark and at 4° C.

Procedure. All the following steps are conducted at room temperature unless it is specifically indicated. All ELISA plate washings are performed by rinsing the plate with tap water three times, followed by one TBST rinse. Pat plate dry with paper towels.

A. Cell Seeding:

1. The cells, grown in tissue culture dish (Corning 25020–100) to 80–90% confluence, are harvested with Trypsin-EDTA (0.25%, 0.5 ml/D-100, GIBCO). 2. Resuspend the cells in fresh DMEM+10% FBS+2 mM L-Glutamine, and transfer to 96-well tissue culture plate (Corning, 25806-96) at 20,000 cells/well (100 μl/well). Incubate for 1 day then replace medium to serum-free medium (90/μl) and incubate in 5% $CO_2$ and 37° C. overnight.

B. ELISA Plate Coating and Blocking:

1. Coat the ELISA plate (Corning 25805-96) with Anti-IGF-1R Antibody at 0.5 μg/well in 100 μl PBS at least 2 hours.

2. Remove the coating solution, and replace with 100 μl Blocking Buffer, and shake for 30 minutes. Remove the blocking buffer and wash the plate just before adding lysate.

C. Assay Procedures:

1. The drugs are tested in serum-free condition.

2. Dilute drug stock (in 100% DMSO) 1:10 with DMEM in 96-well poly-propylene plate, and transfer 10 μl/well of this solution to the cells to achieve final drug dilution 1:100, and final DMSO concentration of 1.0%. Incubate the cells in 5% $CO_2$ at 37° C. for 2 hours.

3. Prepare fresh cell lysis buffer (HNTG*)

| | |
|---|---|
| HNTG | 2 ml |
| EDTA | 0.1 ml |
| $Na_3VO_4$ | 0.1 ml |
| $Na_4(P_2O_7)$ | 0.1 ml |
| $H_2O$ | 7.3 ml |

4. After drug incubation for two hours, transfer 10 μl/well of 200 nM IGF-1 Ligand in PBS to the cells (Final Conc.=20 nM), and incubate at 5% $CO_2$ at 37° C. for 10 minutes.

5. Remove media and add 100 μl/well HNTG* and shake for 10 minutes. Look at cells under microscope to see if they are adequately lysed.

6. Use a 12-channel pipette to scrape the cells from the plate, and homogenize the lysate by repeat aspiration and dispense. Transfer all the lysate to the antibody coated ELISA plate, and shake for 1 hour.

7. Remove the lysate, wash the plate, transfer anti-pTyr (1:3,000 with TBST) 100 μl/well, and shake for 30 minutes.

8. Remove anti-pTyr, wash the plate, transfer Tago (1:3,000 with TBST) 100 μl/well, and shake for 30 minutes.

9. Remove detection antibody, wash the plate, and transfer fresh ABTS/H2O2 (1.2 µl $H_2O_2$ to 10 ml ABTS) 100 µl/well to the plate to start color development.

10. Measure OD at 410 nm with a reference wavelength of 630 nm in Dynatec MR5000.

e. EGF Receptor ELISA

EGF Receptor kinase activity in cells genetically engineered to express human EGF-R is measured as described below:

Materials and Reagents. The following materials and reagents are used
- a. EGF Ligand: stock concentration=16.5 µM; EGF 201, TOYOBO, Co., Ltd. Japan.
- b. 05–101 (UBI) (a monoclonal antibody recognizing an EGFR extracellular domain).
- c. Anti-phosphotyosine antibody (anti-Ptyr) (polyclonal).
- d. Detection antibody: Goat anti-rabbit lgG horse radish peroxidase conjugate, TAGO, Inc., Burlingame, Calif.
- e. TBST buffer:

| Tris-HCl, pH 7 | 50 mM |
|---|---|
| NaCl | 150 mM |
| Triton X-100 | 0.1 | f. HNTG 5× stock:

| HEPES | 0.1M |
|---|---|
| NaCl | 0.75M |
| Glycerol | 50 |
| Triton X-100 | 1.0% | g. ABTS stock:

| Citric Acid | 100 mM |
|---|---|
| $Na_2HPO_4$ | 250 mM |
| HCl, conc. | 4.0 pH |
| ABTS* | 0.5 mg/ml |

Keep solution in dark at 4° C. until used.

h. Stock reagents of:
 EDTA 100 mM pH 7.0
 $Na_3VO_4$ 0.5 M
 $Na_4(P_2O_7)$ 0.2 M Procedure. The following protocol was used:

A. Pre-coat ELISA Plate

1. Coat ELISA plates-(Corning, 96 well, Cat. #25805-96) with 05-101 antibody at 0.5 µg per well in PBS, 150 µl final volume/well, and store overnight at 4° C. Coated plates are good for up to 10 days when stored at 4° C.

2. On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.

B. Seeding Cells

1. NIH 3T3/C7 cell line (Honegger, et al., Cell 51:199–209, 1987) can be use for this assay.

2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm, and once at room temperature for 5 minutes.

3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µl per well, in a 96 well microtiter plate. Incubate seeded cells in 5% $CO_2$ at 37° C. for about 40 hours.

C. Assay Procedures.

1. Check seeded cells for contamination using an inverted microscope. Dilute drug stock (10 mg/ml in DMSO) 1:10 in DMEM medium, then transfer 5 µl to a test well for a final drug dilution of 1:200 and a final DMSO concentration of 1%. Control wells receive DMSO alone. Incubate in 5% $CO_2$ at 37° C. for one hour.

2. Prepare EGF ligand: dilute stock EGF in DMEM so that upon transfer of 10 µl dilute EGF (1:12 dilution), 25 nM final concentration is attained.

3. Prepare fresh 10 ml HNTG* sufficient for 100 µl per well wherein HNTG* comprises: HNTG stock (2.0 ml), milli-Q $H_2O$ (7.3 ml), EDTA, 100 mM, pH 7.0 (0.5 ml), $Na_3VO_4$ 0.5 M (0.1 ml) and $Na_4(P_2O_7)$, 0.2 M (0.1 ml).

4. Place on ice.

5. After two hours incubation with drug, add prepared EGF ligand to cells, 10 µl per well, to yield a final concentration of 25 nM. Control wells receive DMEM alone. Incubate, shaking, at room temperature, for 5 minutes.

6. Remove drug, EGF, and DMEM. Wash cells twice with PBS. Transfer HNTG* to cells, 100 µl per well. Place on ice for 5 minutes. Meanwhile, remove blocking buffer from other ELISA plate and wash with TBST as described above.

7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

8. Remove lysate and wash 4 times with TBST. Transfer freshly diluted anti-Ptyr antibody to ELISA plate at 100 µl per well. Incubate shaking at room temperature for 30 minutes in the presence of the anti-Ptyr antiserum (1:3000 dilution in TBST).

9. Remove the anti-Ptyr antibody and wash 4 times with TBST. Transfer the freshly diluted TAGO 30 anti-rabbit IgG antibody to the ELISA plate at 100 µl per well. Incubate shaking at room temperature for 30 minutes (anti-rabbit IgG antibody: 1:3000 dilution in TBST).

10. Remove detection antibody and-wash 4 times with TBST. Transfer freshly prepared ABTS/$H_2O_2$ solution to ELISA plate, 100 µl per well. Incubate at room temperature for 20 minutes. ABTS/$H_2O_2$ solution: 1.2 µl 30% $H_2O_2$ in 10 ml ABTS stock.

11. Stop reaction by adding 50 µl 5N $H_2SO_4$ (optional), and determine O.D. at 410 nm.

12. The maximal phosphotyrosine signal is determined by subtracting the value of the negative controls from the positive controls. The percent inhibition of phosphotyrosine content for extract-containing wells is then calculated, after subtraction of the negative controls.

2. Cellular/Biologic Assays

Assay 1: PDGF-Induced BrdU Incorporation Assay

Materials and Reagents:
 (1) PDGF: human PDGF B/B; 1276-956, Boehringer Mannheim, Germany
 (2) BrdU Labeling Reagent: 10 mM, in PBS (pH7.4), Cat. No. 1 647 229, Boehringer Mannheim, Germany.

(3) FixDenat: fixation solution (ready to use), Cat. No. 1 647 229, Boehringer Mannheim, Germany.

(4) Anti-BrdU-POD: mouse monoclonal antibody conjugated with peroxidase, Cat. No. 1 647 229, Boehringer Mannheim, Germany.

(5) TMB Substrate Solution: tetramethylbenzidine (TMB), ready to use, Cat. No. 1 647 229, Boehringer Mannheim, Germany.

(6) PBS Washing Solution: 1×PBS, pH 7.4, made in house.

(7) Albumin, Bovine (BSA): fraction V powder; A-8551, Sigma Chemical Co., USA.

(8) 3T3 cell line genetically engineered to express human PDGF-R.

Protocol (1) Cells are seeded at 8000 cells/well in DMEM, 10% CS, 2 mM Gln in a 96 well plate. Cells are incubated overnight at 37° C. in 5% $CO_2$.

(2) After 24 hours, the cells are washed with PBS, and then are serum starved in serum free medium (0%CS DMEM with 0.1% BSA) for 24 hours.

(3) On day 3, ligand (PDGF=3.8 nM, prepared in DMEM with 0.1% BSA) and test compounds are added to the cells simultaneously. The negative control wells receive serum free DMEM with 0.1% BSA only; the positive control cells receive the ligand (PDGF) but no test compound. Test compounds are prepared in serum free DMEM with ligand in a 96 well plate, and serially diluted for 7 test concentrations.

(4) After 20 hours of ligand activation, diluted BrdU labeling reagent (1:100 in DMEM, 0.1% BSA) is added and the cells are incubated with BrdU (final concentration=10 $\mu$M) for 1.5 hours.

(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 $\mu$l/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

Assay 2: EGF-Induced BrdU Incorporation Assay

Materials and Reagents (1) EGF: mouse EGF, 201; Toyobo,Co., Ltd. Japan (2) BrdU Labeling Reagent: 10 mM, in PBS (pH7.4), Cat. No. 1 647 229, Boehringer Mannheim, Germany.

(3) FixDenat: fixation solution (ready to use), Cat. No. 1 647 229, Boehringer Mannheim, Germany.

(4) Anti-BrdU-POD: mouse monoclonal antibody conjugated with peroxidase, Cat. No. 1 647 229, Boehringer Mannheim, Germany.

(5) TMB Substrate Solution: tetramethylbenzidine (TMB), ready to use, Cat. No. 1 647 229, Boehringer Mannheim, Germany.

(6) PBS Washing Solution: 1×PBS, pH 7.4, made in house.

(7) Albumin, Bovine (BSA): fraction V powder; A-8551, Sigma Chemical Co., USA.

(8) 3T3 cell line genetically engineered to express human EGF-R.

Protocol (1) Cells are seeded at 8000 cells/well in 10% CS, 2 mM Gln in DMEM, in a 96 well plate. Cells are incubated overnight at 37° C. in 5% $CO_2$.

(2) After 24 hours, the cells are washed with PBS, and then are serum starved in serum free medium (0%CS DMEM with 0.16 BSA) for 24 hours.

(3) On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.

(4) After 20 hours of ligand activation, diluted BrdU labeling reagent (1:100 in DMEM, 0.1% BSA) is added and the cells are incubated with BrdU (final concentration=10 $\mu$M) for 1.5 hours.

(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 $\mu$l/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

Assay 3: EGF-Induced Her2 -Driven BrdU Incorporation

Materials and Reagents:
(1) EGF: mouse EGF, 201; Toyobo,Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution : 1×PBS, pH 7.4, made in house.
(7) Albumin, Bovine (BSA): fraction V powder; A-8551, Sigma Chemical Co., USA.
(8) 3T3 cell line engineered to express a chimeric receptor having the extra-cellular domain of EGF-R and the intra-cellular domain of Her2.

Protocol:
(1) Cells are seeded at 8000 cells/well in DMEM, 10% CS, 2 mM Gln in a 96-well plate. Cells are incubated overnight at 37° in 5% $CO_2$.
(2) After 24 hours, the cells are washed with PBS, and then are serum starved in serum free medium (0%CS DMEM with 0.1% BSA) for 24 hours.
(3) On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.
(4) After 20 hours of ligand activation, diluted BrdU labeling reagent (1:100 in DMEM, 0.1% BSA) is added and the cells are incubated with BrdU (final concentration =10 $\mu$M) for 1.5 hours.
(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 $\mu$l/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

Assay 4: IGF1-Induced BrdU Incorporation Assay

Materials and Reagents:
(1) IGF1 Ligand: human, recombinant; G511, Promega Corp, USA.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1×PBS, pH 7.4, made in house.
(7) Albumin, Bovine (BSA): fraction V powder; A-8551, Sigma Chemical Co., USA.
(8) 3T3 cell line genetically engineered to express human IGF-1 receptor.

Protocol:
(1) Cells are seeded at 8000 cells/well in DMEM, 10% CS, 2 mM Gln in a 96-well plate. Cells are incubated overnight at 37° C. in 5% $CO_2$.
(2) After 24 hours, the cells are washed with PBS, and then are serum starved in serum free medium (0%CS DMEM with 0.1% BSA) for 24 hours.
(3) On day 3, ligand (IGF1=3.3 nM, prepared in DMEM with 0.1% BSA) and test compounds are added to the cells simultaneously. The negative control wells receive serum free DMEM with 0.1% BSA only; the positive control cells receive the ligand (IGF1) but no test compound. Test compounds are prepared in serum free DMEM with ligand in a 96 well plate, and serially diluted for 7 test concentrations.
(4) After 16 hours of ligand activation, diluted BrdU labeling reagent (1:100 in DMEM, 0.1% BSA) is added and the cells are incubated with BrdU (final concentration=10 $\mu$M) for 1.5 hours.
(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 $\mu$l/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

g. HUV-EC-C Assay

The following protocol may also be used to measure a compound's activity against PDGF-R, FGF-R or Flk-1/KDR, all of which are naturally expressed by HUV-EC cells.

DAY 0

1. Wash and trypsinize HUV-EC-C cells (human umbilical vein endothelial cells, (American Type Culture Collection; catalogue no. 1730 CRL). Wash with Dulbecco's phosphate-buffered saline (D-PBS; obtained from Gibco BRL; catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 ml/25–30 $cm^2$ of tissue culture flask for about 5 minutes at 37° C. After cells have detached from the flask, add an equal volume of assay medium and transfer to a 50 ml sterile centrifuge tube (Fisher Scientific; catalogue no. 05-539-6).

2. Wash the cells with about 35 ml assay medium in-the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 $cm^2$ of tissue culture flask. Assay medium consists of F12K medium (Gibco BRL; catalogue no. 21127-014) +0.5% heat-inactivated fetal bovine serum. Count the cells with a Coulter Counter®v Coulter Electronics, Inc.) and add assay medium to the cells to obtain a concentration of $0.8–1.0\times10^5$ cells/ml.

3. Add cells to 96-well flat-bottom plates at 100 μl/well or $0.8–1.0\times10^4$ cells/well; incubate ~24 h at 37° C., 5% $CO_2$.

DAY 1

1. Make up two-fold drug titrations in separate 96-well plates, generally 50 μM on down to 0 μM. Use the same assay medium as mentioned in day 0, step 2 above. Titrations are made by adding 90 μl/well of drug at 200 μM (4×the final well concentration) to the top well of a particular plate column. Since the stock drug concentration is usually 20 mM in DMSO, the 200 μM drug concentration contains 2% DMSO.

Therefore, diluent made up to 2% DMSO in assay medium (F12K+0.5% fetal bovine serum) is used as diluent for the drug titrations in order to dilute the drug but keep the DMSO concentration constant. Add this diluent to the remaining wells in the column at 60 μl/well. Take 60 μl from the 120 μl of 200 AM drug dilution in the top well of the column and mix with the 60 μl in the second well of the column. Take 60 μl from this well and mix with the 60 μl in the third well of the column, and so on until two-fold titrations are completed. When the next-to-the-last well is mixed, take 60 μl of the 120 μl in this well and discard it. Leave the last well with 60 μl of DMSO/media diluent as a non-drug-containing control. Make 9 columns of titrated drug, enough for triplicate wells each for 1) VEGF (obtained from Pepro Tech Inc., catalogue no. 100-200, 2) endothelial cell growth factor (ECGF) (also known as acidic fibroblast growth factor, or aFGF) (obtained from Boehringer Mannheim Biochemica, catalogue no. 1439 600); or, 3) human PDGF B/B (1276-956, Boehringer Mannheim, Germany) and assay media control. ECGF comes as a preparation with sodium heparin.

2. Transfer 50 μl/well of the drug dilutions to the 96-well assay plates containing the $0.8–1.0\times10^4$ cells/100 μl/well of the HUV-EC-C cells from day 0 and incubate ~2 h at 37° C., 5% $CO_2$.

3. In triplicate, add 50 μl/well of 80 μg/ml VEGF, 20 ng/ml ECGF, or media control to each drug condition. As with the drugs, the growth factor concentrations are 4× the desired final concentration. Use the assay media from day 0 step 2 to make the concentrations of growth factors. Incubate approximately 24 hours at 37° C., 5% $CO_2$. Each well will have 50 μl drug dilution, 50 μl growth factor or media, and 100 μl cells, 200 μl/well total. Thus the 4× concentrations of drugs and growth factors become 1×once everything has been added to the wells.

DAY 2

1. Add $^3$H-thymidine (Amersham; catalogue no. TRK-686) at 1 μCi/well (10 μl/well of 100 μCi/ml solution made up in RPMI media +10% heat-inactivated fetal bovine serum) and incubate ~24 h at 37° C., 5% $CO_2$. RPMI was obtained from Gibco BRL, catalogue no. 11875-051.

DAY 3

1. Freeze plates overnight at −20° C.

DAY 4

1. Thaw plates and harvest with a 96-well plate harvester (Tomtec Harvester 96$^{(R)}$) onto filter mats (Wallac; catalogue no. 1205-401); read counts on a Wallac Betaplate$^{(TM)}$ liquid scintillation counter.

C. In Vivo Animal Models

1. Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC #CCL 107), A375 cells (melanoma, ATCC #CRL 1619), A431 cells (epidermoid carcinoma, ATCC #CRL 1555), Calu 6 cells (lung, ATCC #HTB 56), PC3 cells (prostate, ATCC #CRL 1435) and NIH 3T3 fibroblasts genetically engineered to overexpress EGFR, PDGFR, IGF-1R or any other test kinase.

The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, NY) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, $2-10 \times 10^6$ cells/animal) Tumor growth is measured over 3 to 6 weeks using venier calipers. Tumor volumes are calculated as a product of length×width×height unless otherwise indicated. P values are calculated using the Students' t-test. Test compounds in 50–100 μL excipient (DMSO, or VPD:D5W) was delivered by IP injection at different concentrations generally starting at day one after implantation.

2. Tumor Invasion Model

The following tumor invasion model has been developed and maybe used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells was performed in a laminar flow hood. For anesthesia, Xylazine/Ketamine Cocktail (100 mg/kg ketamine and 5 mg/kg) are administered intraperitoneally. A midline incision is done to expose the abdominal cavity (approximately 1.5 cm in length) to inject $10^7$ tumor cells in a volume of 100 μl medium. The cells are injected either into the duodenal lobe of the pancreas or under the serosa of the colon. The peritoneum and muscles are closed with a 6–0 silk continuous suture and the skin was closed by using would clips. Animals are observed daily.

Analysis

After 2–6 weeks, depending on gross observations of the animals, the mice are sacrificed, and the local tumor metastases, to various organs (lung, liver, brain, stomach, spleen, heart, muscle) are excised and analyzed (measurements of tumor size, grade of invasion, immunochemistry, and in situ hybridization).

D. EXAMPLES OF ASSAYS

The following are examples of the results of specific assays used to evaluate the activity of the compounds of this invention.

The assays shown are exemplary only and are not to be construed as limiting in any manner.

1. Inhibition of Ligand-stimulated DNA Synthesis

The following example illustrates the ability of the compounds of the invention to inhibit FGFR-stimulated and PDGFR-stimulated DNA synthesis in cells. DNA synthesis is required for many of the activities of FGFP and PDGFR including, but not limited to, cell proliferation. Uridine is added in one set of samples to overcome any contribution made by inhibition of DHOD and just evaluate the inhibition of PDGFR or FGFR signaling. (See Greene, et al., *Biochem. Pharmacol.*, 50(6):861 (1995), Nair, et al., *Immunology Letters*, 47:171 (1995)).

MATERIALS AND METHODS (1) EGF: mouse EGF, 201; Toyobo,Co., Ltd. Japan; PDGF, Boehringer Mannheim, Germany; FGF, Gibco.
(2) BrdU Labeling Reagent: 10 mM, in PBS (pH7.4) Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1×phosphate buffered saline, pH 7.4
(7) Albumin, Bovine (BSA): fraction V powder; A-8551, Sigma Chemical Co., USA.
(8) NIH3T3 clone C7 (3T3/EGFRc7)(Honegger et al., Cell 51:199–209, 1987)) engineered to over-express human EGF receptor.

These cells natively express FGFR and PDGFR.

PROTOCOL (1) 3T3/EGFRc7 cells were seeded at 8000 cells/well in DMEM, 10% CS, 2 mM Gln in a 96 well plate. Cells are incubated overnight at 37 degrees C. in 5% $CO_2$.
(2) After 24 hours, the cells were washed with PBS, and then serum starved in serum free medium (0%CS DMEM with 0.1% BSA) for 24 hours.
(3) On day 3, ligand (2n EGF or 1.5 nM FGF or 3.8 nM PDGF) prepared in DMEM with 0.1% BSA and 30 μM (final concentration) uridine) and test compound was added to the cells simultaneously.

The negative control wells received serum free DMEM with 0.1% BSA only; the positive control cells received ligand but no test compound. Test compound was prepared in serum free DMEM with ligand in a 96 well plate, and serially diluted for 7 test concentrations.

(4) After 20 hours of ligand activation, diluted BrdU labeling reagent (1:100 in DMEM, 0.1% BSA) was added and the cells were incubated with BrdU (final concentration=10 μM) for 1.5 hours.
(5) After incubation with labeling reagent, the medium was removed by decanting and tapping the inverted plate on a paper towel. FixDenat solution was added (50 μl/well) and the plates incubated at room temperature for 45 minutes on a plate shaker.
(6) The FixDenat solution was thoroughly removed by decanting and tapping the inverted plate on a paper towel. Milk is added (5% dehydrated milk in PBS, 200 μl/well) as a blocking solution and the plate was incubated for 30 minutes at room temperature on a plate shaker.
(7) The blocking solution was removed by decanting and the wells were washed once with PBS. Anti-BrdU-POD solution (1:100 dilution in PBS, 1% BSA) was added (100 μl/well) and the plate was incubated for 90 minutes at room temperature on a plate shaker.
(8) The antibody conjugate was thoroughly removed by decanting and rinsing the wells 5 times with PBS, and the plate dried by inverting and tapping on a paper towel.
(9) TMB substrate solution was added (100 μl/well) and incubated for 20 minutes at room temperature on a plate shaker until color development was sufficient for photometric detection.
(10) The absorbance of the samples was measured at 410 nm (in "dual wavelength" mode with a filter reading at 490 nm, as a reference wavelength) on a Dynatech ELISA plate reader.

RESULTS

In a first experiment, the activity of leflunomide, its metabolite and a compound of this invention are compared in their ability to inhibit FGF induced DNA synthesis alone or with added uridine. As shown in Table 1 below, the ability of the metabolite to inhibit DNA synthesis is completely abolished by the addition of uridine and that of leflunomide reduced, demonstrating that the inhibitory effect is due to inhibition of DHOD, not inhibition of FGFR signaling. In contrast, the inhibitory activity of claimed compound in not decreased, and is even slightly increased, demonstrating that it is inhibiting FGFR signaling. Similar experiments were conducted using PDGF stimulation with similar results. Also tested was the known DHOD inhibitor brequinar which inhibited DNA synthesis in the absence of uridine (IC50=1.6 $\mu$M) and was inactive in the presence of uridine (IC50=>100 $\mu$M)

TABLE 1

| Compound | IC50 − uridine | IC50 + uridine |
|---|---|---|
| leflunomide | 20 $\mu$M | 80 $\mu$M |
| A771726 | 20 $\mu$M | >100 $\mu$M |
| 3-Methyl-4-[4-(trifluoromethyl)phenyl-aminocarbonyl]isoxazole (cmpd. 1) | 85 $\mu$M | 70 $\mu$M |

In another experiment, several of the compounds of this invention were tested for their ability to inhibit DNA synthesis induced by FGF, PDGF and EGF. The results, shown in Table 2 below, indicate that the compounds of the invention are selective for inhibition of FGF and PDGF induced signaling compared to EGF signaling.

TABLE 2

| Compound | PDGF-induced | FGF-induced | EGF-induced |
|---|---|---|---|
| 3-Methyl-4-[4-(trifluoromethyl)phenylaminocarbonyl]pyrazole (cmpd. 2) | 95 $\mu$M | >100 $\mu$M | >100 $\mu$M |
| 3,5-Dimethyl-4-[4-(trifluoromethyl)phenylaminocarbonyl]isoxazole (cmpd. 21) | >100 $\mu$M | >100 $\mu$M | >100 $\mu$M |
| 3-Methyl-4-[4-(trifluoromethyl)phenylaminocarbonyl]isoxazole (cmpd. 1) | 90 $\mu$M | 65 $\mu$M | >100 $\mu$M |

2. Inhibition of Tumor Growth in vivo

The following example demonstrates the ability of Cmpd. 1 to inhibit the in vivo growth of tumors characterized by inappropriate FGFR and/or PDGFR activity. The FGFR expressing cells are from two glioblastomas (C6, ATCC CRL 107, Powell and Klagsbrun, *Exp. Cell Res.*, 209:224 (1993); for PDGER, see Strawn, et al., *J. Biol. Chem.*, 269:21215 (1995).

MATERIALS AND METHODS

Female athymic mice (BALB/c, nu/nu) were obtained from Simonsen Laboratories (Gilroy, Calif.). All animals were maintained under clean-room conditions in Microisolator cages with Alpha-dri bedding. They received sterile rodent chow and water ad libitum.

Cell lines were grown in Ham's F10 plus 5% fetal bovine serum (FBS) and 2 mM glutamine (GLN). All cell culture media, glutamine, and fetal bovine serum were purchased from Gibco Life Technologies (Grand Island, N.Y.) unless otherwise specified. All cells were grown in a humid atmosphere of 90–95% air and 5–10% $CO_2$ at 37° C. All cell lines were routinely subcultured twice a week and were negative for mycoplasma as determined by the Mycotect method (Gibco).

Cells were harvested at or near confluency with 0.05% Trypsin-EDTA and pelleted at 450×g for 10 min. Pellets were resuspended in sterile PBS or media (without FBS) and the cells were implanted into the hindflank of the mice (8–10 mice per group $3 \times 10^6$ cells/animal). Tumor growth was measured over 3 weeks using venier calipers. Tumor volumes were calculated as a product of length×width×height unless otherwise indicated. P values were calculated using the Students' t-test. Cmpd. 1 in 50 $\mu$L excipient (DMSO) was delivered by IP bolus injection daily.

RESULTS

The results of the subcutaneous xenograft experiment, shown in Table 3 below, demonstrates that administration of Cmpd. 1 significantly inhibited the tumor growth in vivo and had no toxic effect at the dose tested.

TABLE 3

| Treatment | Day | inhibition (% of control) | mortality | p-value |
|---|---|---|---|---|
| DMSO alone | 20 | — | 0 | — |
| 30 mg/kg/day (cmpd. 1) | 8 | 34 | 0 | 0.0158 |
|  | 10 | 42 | 0 | 0.0034 |
|  | 13 | 48 | 0 | 0.0520 |
|  | 15 | 47 | 0 | 0.0392 |
|  | 17 | 50 | 0 | 0.0188 |
|  | 20 | 52 | 0 | 0.0064 |

3. Inhibition of Tumor Growth and Metastasis in vivo

The following example can be used to test the ability of the compounds of the invention to inhibit growth and metastasis of a tumor cell line expressing FGFR and PDGFR (C6 cells).

MATERIALS AND METHODS

Ten to 12 week old athymic Balb/c nu/nu mice are obtained from Simonsen Laboratory (Gilroy, Calif.) and maintained in a pathogen-free environment throughout the experiments.

C6 cells (ATCC CCL 107) are grown and maintained in F-10 medium (Life Technologies, Inc. Grand Island, N.Y.) supplemented with 10% fetal bovine serum, 2 mM glutamine in a 5% $CO_2$ environment. Approximately 80% confluent cultures are harvested by brief trypsinization (0.0625% trypsin-0.25 mM EDTA in Cell Dissociation Medium) (Life Technologies) and resuspended at a final concentration of $8 \times 10^7$ cells per ml in magnesium and calcium free phosphate buffered saline for implantation. Cell viability is determined by Trypan blue exclusion and found to be >95%.

On the day of implantation, animals are anesthetized with either isoflurane or Ketaset and Rompun and the abdomen is prepared for sterile surgery. A small abdominal incision is made and the ascending colon identified. The gut is then placed on strips of sterile gauze before injection. Two million viable tumor cells in 0.025 ml PBS are injected under the serosa into the muscularis/submuscularis by means of a sterile tuberculin syringe and a 27 gauge needle. Cells are injected so as to visibly infiltrate between the submucosal and subserosal tissues. The serosal surface at the injection site is dabbed gently with 70% isopropyl alcohol pads to kill tumor cells that may have escaped. The organs are replace in situ. The abdominal wall is closed with continuous nylon sutures. The outer skin is then closed using wound clips which are removed seven days post implantation.

To ensure that cell implantation is properly performed, after 7 days, several control animals are euthanized by cerebral dislocation, the abdominal organs and thorax examined for the presence of macroscopic "primary" colonic tumors and metastases. Pilot studies demonstrated that at this time intracolonic tumors of approximately 5 to 7 mm$^3$ are present without peritoneal spread of tumor after injection of C6 cells.

One day following implantation of cells, animals are treated once daily intraperitoneally with either MCTA at 20 mg/kg/day in VPD:D5W or vehicle alone in a 0.1 ml bolus. The health of the animals is monitored daily and if signs of severe discomfort or pain is observed or the animal is deemed to be moribund, animals are sacrificed humanely. Dosing of the animals continued until all surviving animals in the experiment are deemed moribund. When possible, the local tumor growth on the colon is measured and the major organs such as lung, heart, spleen, liver and kidney are resected from moribund animals and submitted for histopathological analysis.

E. Measurement of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques (Mossman, 1983, *J. Immunol. Methods*, 65:55–63), by measuring the amount of LDH released (Korzeniewski and Callewaert, 1983, *J. Immunol. Methods*, 64:313; Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

CONCLUSION

Thus, it will be appreciated that the compounds, methods and pharmacological compositions of the present invention modulate PTK activity and therefore to be effective as therapeutic agents against PTK-related disorders.

Although certain embodiments and examples have been used to describe the present invention, it will be apparent to those skilled in the art that changes to the embodiments and examples shown may be made without departing from the scope and spirit of the invention.

Other embodiments are within the following claims.

What is claimed is:

1. A heteroarylcarboxamide compound having the following chemical structure:

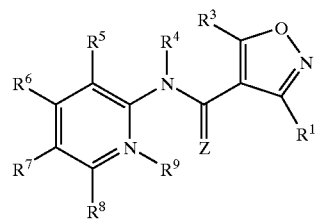

wherein:

$R^1$ is selected from the group consisting of alkyl, cycloalkyl, alkenyl, alkynyl, aryl, heteroaryl and heteroalicyclic;

$R^3$ is selected from the group consisting of hydrogen, cycloalkyl, alkenyl, alkynyl, heteroaryl and heteroalicyclic;

Z is selected from the group consisting of oxygen and sulfur;

$R^4$ is selected from the group consisting of hydrogen, alkyl, cycloalkyl, alkenyl, alkynyl, aryl heteroaryl, heteroalicyclic, sulfonyl, trihalomethanesulfonyl, hydroxy, alkoxy and C-carboxy;

$R^5$, $R^6$, $R^7$, $R^8$ and $R^9$ are independently selected from the group consisting of hydrogen, alkyl, trihaloalkyl, alkenyl, alkynyl, cycycloalkyl, aryl, heteroaryl, heteroalicyclic, hydroxy, alkoxy, cycloalkoxy, aryloxy, heteroaryloxy, heteroalicycloxy, thiohydroxy, thioalkyoxy, thiocycloalkoxy, thioheteraryloxy, thioheteralicycloxy, halo, nitro, cyano, C-O-carbamyl, N-carbamyl, O-thiocarbamyl, N-thiocarbamyl, silyl, phosphonyl, C-carboxy, O-carboxy, N-amido, C-amido, sulfinyl, sulfonyl, S-sulfonamido, N-sulfonamido, trihalomethanesulfonyl, guanyl, guanidino, trihalomethanesulfonamido, amino and —$NR^{13}R^{14}$, $R^{13}$ and $R^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring containing at least one nitrogen;

and physiologically acceptable salts thereof.

2. The compound or salt of claim 1 wherein $R^1$ is selected from the group consisting of alkyl, cycloalkyl, alkenyl and alkynyl.

3. The compound or salt of claim 2 wherein $R^3$ is selected from the group consisting of hydrogen, and cycloalkyl.

4. The compound or salt of claim 3 wherein $R^4$ is hydrogen.

5. The compound or salt of claim 4 wherein Z is oxygen.

6. The compound or salt of claim 5 wherein $R^5$, $R^6$, $R^7$, $R^8$ and $R^9$ are hydrogen.

7. The compound or salt of claim 6 wherein $R^7$ is selected from the group consisting of trihalomethyl and trihalomethanesulfonyl.

8. The compound or salt of claim 7 wherein $R^5$, $R^6$, $R^7$, $R^8$ and $R^9$ are hydrogen.

9. The compound or salt of claim 8 wherein $R^6$ and $R^7$ combine to form a methylenedioxy or a 1,3-dioxano group.

10. The compound or salt of claim 8 wherein $R^3$ is hydrogen.

11. A pharmacological composition of said compound of claim 1.

12. A method for the treatment or prevention of a disorder characterized by inappropriate protein tyrosine kinase activity comprising administering to an organism afflicted with such a disorder a therapeutically effective amount of one of more of said compounds of claim 1 or a physiologically acceptable salt thereof.

13. The method of claim 12 wherein said therapeutically effective amount of said compound of claim 1 is administered as a pharmacological composition.

14. The method of claim 12 wherein said organism is a mammal.

15. The method of claim 14 wherein said mammal is a human.

16. The method of claim 12 wherein said disorder comprises a cancer.

17. The method of claim 16 wherein said cancer is selected from the group consisting of brain cancer, colon cancer, prostate cancer, kidney cancer, breast cancer, lung cancer, salivary gland cancer, oral cancer, pancreatic cancer, bladder cancer, Kaposi's sarcoma, melanoma and ovarian cancer.

18. The method of claim 12 wherein said disorder comprises a skeletal disorder.

19. The method of claim 12 wherein said disorder comprises a fibrotic disorder.

20. The method of claim 12 wherein said disorder comprises a blood vessel proliferative disorder.

21. The method of claim 19 wherein said fibrotic disorder comprises restinosis, hepatic cirrhosis, glomerular sclerosis, interstitial nephritis, interstitial pulmonary fibrosis, atherosclerosis, wound scarring and scleroderma.

22. A method of inhibiting the metastasis of a cancer comprising administering to an organism in need of such inhibition a therapeutically effective amount of one or more compounds of claim 1.

23. The method of claim 22 wherein said therapeutically effective amount of one or more of the compounds is administered as a pharmacological composition.

24. The method of claim 23 wherein said cancer comprises colon cancer, prostate cancer, pancreatic cancer, Kaposi's sarcoma, ovarian cancer, breast cancer and gliomas.

* * * * *